United States Patent [19]
Janjic et al.

[11] Patent Number: 5,859,228
[45] Date of Patent: Jan. 12, 1999

[54] VASCULAR ENDOTHELIAL GROWTH FACTOR (VEGF) NUCLEIC ACID LIGAND COMPLEXES

[75] Inventors: Nebojsa Janjic; Larry Gold, both of Boulder; Paul Schmidt, Niwot, all of Colo.

[73] Assignee: NeXstar Pharmaceuticals, Inc., Boulder, Colo.

[21] Appl. No.: 739,109

[22] Filed: Oct. 25, 1996

Related U.S. Application Data

[63] Continuation-in-part of Ser. No. 434,465, May 4, 1995.
[51] Int. Cl.$^6$ .......................... C07H 21/02; C07H 21/04; A16K 31/70
[52] U.S. Cl. .............................. 536/24.3; 514/44
[58] Field of Search .................... 435/6, 91.2; 536/25.4, 536/24.3; 935/77, 78; 514/44

[56] References Cited

U.S. PATENT DOCUMENTS

| | | | |
|---|---|---|---|
| 4,861,597 | 8/1989 | Kida et al. | 424/450 |
| 4,904,582 | 2/1990 | Tullis | 435/6 |
| 4,997,652 | 3/1991 | Wong | 424/428 |
| 5,149,794 | 9/1992 | Yatvin et al. | 536/23.1 |
| 5,245,022 | 9/1993 | Weis et al. | 536/24.5 |
| 5,270,163 | 12/1993 | Gold et al. | 435/6 |
| 5,283,185 | 2/1994 | Epand et al. | 435/172.3 |
| 5,459,015 | 10/1995 | Janjic et al. | 435/6 |
| 5,475,096 | 12/1995 | Gold et al. | 435/6 |
| 5,595,877 | 1/1997 | Gold et al. | 435/6 |
| 5,635,487 | 6/1997 | Wolff et al. | 514/44 |

FOREIGN PATENT DOCUMENTS

| | | |
|---|---|---|
| 0462145 | 4/1994 | European Pat. Off. . |
| 2 183 661 A | 6/1987 | United Kingdom . |
| WO89/06694 | 7/1989 | WIPO . |
| 9010448 | 9/1990 | WIPO . |
| 9114696 | 10/1991 | WIPO . |
| WO92/14843 | 9/1992 | WIPO . |
| 9401448 | 1/1994 | WIPO . |
| 9415619 | 7/1994 | WIPO . |
| 9427615 | 12/1994 | WIPO . |
| 9429479 | 12/1994 | WIPO . |
| 9500529 | 1/1995 | WIPO . |
| 9506474 | 3/1995 | WIPO . |
| 9506659 | 3/1995 | WIPO . |
| 9621469 | 7/1996 | WIPO . |

OTHER PUBLICATIONS

Jakeman et al.,*J. Clin. Investig.* 89:244–252 (Jan. 1992) (Last page missing).
Jaschke et al., "Synthesis and properties of oligodeoxyribonucleotide–polyethylene glycol conjugates", Nuc. Acids Res. 22(22):4810–4817, 1994.
MacKellar et al., "Synthesis and physical properties of anti–HIV antisense oligonucleotides bearing terminal lipophilic groups," Nuc. Acids Res. 20(13):3411–3417, 1992.
Shea et al., "Synthesis hybridization properties and antiviral activity of lipid–oligodeoxynucleotide conjugates," Nuc. Acids Res. 18(13):3777–3783, 1990.
Joyce (1989) Gene 82:83.
Joyce & Inoue (1989) Nucleic Acids Research 17:711.
Ellington & Szostak (1990) Abstracts of papers presented at the 1990 meeting on RNA Processing Cold Spring Harbor Laboratory, Cold Spring Harbor, NY. p. 84.
Kinzler & Vogelstein (1989) Nucleic Acids Research 17:3645.
Kramer et al. (1974) J. Mol. Biol. 89:719.
Levisohn & Spiegelman (1969) PNAS USA 63:805.
Levisohn & Spiegelman (1968) PNAS USA 60:866.
Oliphant et al. (1989) Mol. Cell. Biol. 9:2944.
Oliphant & Struhl (1988) Nucleic Acids Research 16:7673.
Oliphant & Struhl (1987) Methods in Enzymology 155:568.
Oliphant et al. (1986) Gene 44:177.
Robertson & Joyce (1990) Nature 844:467.
Thiesen & Bach (1990) Nucleic Acids Research 18:5203.

*Primary Examiner*—Stephanie Zitomer
*Attorney, Agent, or Firm*—Swanson & Bratschun LLC

[57] ABSTRACT

This invention discloses a method for preparing a complex comprised of a VEGF Nucleic Acid Ligand and a Lipophilic Compound by identifying a VEGF Nucleic Acid Ligand by SELEX methodology and associating the VEGF Nucleic Acid Ligand with a Lipophilic Compound. The invention further discloses Complexes comprising one or more VEGF Nucleic Acid Ligands in association with a Lipophilic Compound. The invention further includes a Lipid construct comprising a VEGF Nucleic Acid Ligand or Complex and methods for making the same.

7 Claims, 9 Drawing Sheets

NX-213
SEQ ID NO: 1

Ligand =
5'-TsTsTsTsmAaCaCaCaUrGrAaUmGrAaUmAmGrAaCmGaCaCmGmGmGmGaUmGTsTsTsTsT-3'

FIGURE 1A

Structure =

NX-278
SEQ ID NO: 2

Ligand component =
5'-TsTsTsTsmAaCaCaCaUrGrAaUmAmGrAaUmGrGaUmAmGrAaCmGaCaCmGmGmGaAaCmGmGmGaAaUmGTsTsTsTsT-3'
(VEGF ligand)

Ligand component =
5'-TsTsTsTs mGaUaC mGmGaU mAaCrG mGrAmG aUmGrG rAaCaC mGaUaC mAaCmG TsTsTsTsT-3'
(VEGF ligand)

scNX-213
SEQ ID NO: 4

Ligand =
5'-TsTsTsTsmGaUaCmGmGaUmAaCrGmGrAmGaUmGrGrAaCaCmGaUaCmAaCmGTsTsTsTsT-3'

FIGURE 1D

VASCULAR ENDOTHELIAL GROWTH FACTOR (VEGF) NUCLEIC ACID LIGAND COMPLEXES

RELATED APPLICATIONS

This application is a Continuation-in-Part of U.S. patent application Ser. No. 08/434,465, filed May 4, 1995, entitled "Nucleic Acid Ligand Complexes."

FIELD OF THE INVENTION

This invention relates to a method for preparing a therapeutic or diagnostic Complex comprised of a VEGF Nucleic Acid Ligand and a Lipophilic Compound by identifying a VEGF Nucleic Acid Ligand by SELEX methodology and associating the VEGF Nucleic Acid Ligand with a Lipophilic Compound. The invention further includes a Lipid Construct comprising a VEGF Nucleic Acid Ligand or a Complex comprised of a VEGF Nucleic Acid Ligand and a Lipophilic Compound. The invention further relates to improving the pharmacokinetic properties of a VEGF Nucleic Acid Ligand by associating the VEGF Nucleic Acid Ligand with a Lipophilic Compound to form a Complex. The invention further relates to improving the pharmacokinetic properties of a VEGF Nucleic Acid Ligand by using a Lipid Construct comprising a VEGF Nucleic Acid Ligand or a Complex comprised of a VEGF Nucleic Acid Ligand and a Lipophilic Compound. The invention further relates to a method for targeting additional therapeutic or diagnostic agents to a specific predetermined biological target by associating the agent with a Lipid Construct comprising a VEGF Nucleic Acid Ligand or a Complex comprised of a Nucleic Acid Ligand and Lipophilic Compound, wherein the Nucleic Acid Ligand of a SELEX Target is associated with the exterior of the Lipid Construct. The invention also includes Complexes comprising one or more VEGF Nucleic Acid Ligands in association with a Lipophilic Compound.

BACKGROUND OF THE INVENTION

A. SELEX

The dogma for many years was that nucleic acids had primarily an informational role. Through a method known as Systematic Evolution of Ligands by EXponential enrichment, termed SELEX, it has become clear that nucleic acids have three dimensional structural diversity not unlike proteins. SELEX is a method for the in vitro evolution of nucleic acid molecules with highly specific binding to target molecules and is described in U.S. patent application Ser. No. 07/536,428, filed Jun. 11, 1990, entitled "Systematic Evolution of Ligands by Exponential Enrichment", now abandoned, U.S. patent application Ser. No. 07/714,131, filed Jun. 10, 1991, entitled "Nucleic Acid Ligands", now U.S. Pat. No. 5,475,096, U.S. patent application Ser. No. 07/931,473, filed Aug. 17, 1992, entitled "Methods for Identifying Nucleic Acid Ligands", now U.S. Pat. No. 5,270,163 (see also WO 91/19813), each of which is specifically incorporated by reference herein. Each of these applications, collectively referred to herein as the SELEX Patent Applications, describes a fundamentally novel method for making a Nucleic Acid Ligand to any desired target molecule. The SELEX process provides a class of products which are referred to as Nucleic Acid Ligands, each ligand having a unique sequence, and which has the property of binding specifically to a desired target compound or molecule. Each SELEX-identified Nucleic Acid Ligand is a specific ligand of a given target compound or molecule.

SELEX is based on the unique insight that Nucleic Acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of Nucleic Acids, preferably comprising a segment of randomized sequence, the SELEX method includes steps of contacting the mixture with the target under conditions favorable for binding, partitioning unbound Nucleic Acids from those Nucleic Acids which have bound specifically to target molecules, dissociating the Nucleic Acid-target complexes, amplifying the Nucleic Acids dissociated from the Nucleic Acid-target complexes to yield a ligand-enriched mixture of Nucleic Acids, then reiterating the steps of binding, partitioning, dissociating and amplifying through as many cycles as desired to yield highly specific high affinity Nucleic Acid Ligands to the target molecule.

It has been recognized by the present inventors that the SELEX method demonstrates that Nucleic Acids as chemical compounds can form a wide array of shapes, sizes and configurations, and are capable of a far broader repertoire of binding and other functions than those displayed by Nucleic Acids in biological systems.

The present inventors have recognized that SELEX or SELEX-like processes could be used to identify Nucleic Acids which can facilitate any chosen reaction in a manner similar to that in which Nucleic Acid Ligands can be identified for any given target. In theory, within a Candidate Mixture of approximately $10^{13}$ to $10^{18}$ Nucleic Acids, the present inventors postulate that at least one Nucleic Acid exists with the appropriate shape to facilitate each of a broad variety of physical and chemical interactions.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," describes the use of SELEX in conjunction with gel electrophoresis to select Nucleic Acid molecules with specific structural characteristics, such as bent DNA. U.S. patent application Ser. No. 08/123,935, filed Sep. 17, 1993, entitled "Photoselection of Nucleic Acid Ligands," describes a SELEX based method for selecting Nucleic Acid Ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," abandoned in favor of U.S. patent application Ser. No. 08/443, 957, now U.S. Pat. No. 5,580,737, describes a method for identifying highly specific Nucleic Acid Ligands able to discriminate between closely related molecules, which can be non-peptidic, termed Counter-SELEX. U.S. patent application Ser. No. 08/143,564, filed Oct. 25, 1993, entitled "Systematic Evolution of Ligands by EXponential Enrichment: Solution SELEX," abandoned in favor of U.S. patent application Ser. No. 08/461,069, now U.S. Pat. No. 5,567, 588, describes a SELEX-based method which achieves highly efficient partitioning between oligonucleotides having high and low affinity for a target molecule.

The SELEX method encompasses the identification of high-affinity Nucleic Acid Ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic Acid Ligands containing modified nucleotides are described in U.S. patent application Ser. No. 08/117,991, filed Sep. 8, 1993, entitled "High Affinity Nucleic Acid Ligands Containing Modified Nucleotides," abandoned in favor of U.S. patent application Ser. No. 08/430,709, now U.S. Pat. No. 5,660,985, that describes oligonucleotides containing nucleotide derivatives chemically modified at the 5- and 2'-positions of pyrimidines. U.S. patent application Ser. No. 08/134,028, supra, describes highly specific Nucleic Acid Ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of 2' Modified Pyrimidine Intramolecular Nucleophilic Displacement", describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX," now U.S. Pat. No. 5,637,459, and U.S. patent application Ser. No. 08/234,997, filed Apr. 28, 1994, entitled "Systematic Evolution of Ligands by Exponential Enrichment: Blended SELEX," now U.S. Pat. No. 5,683,867, respectively. These applications allow the combination of the broad array of shapes and other properties, and the efficient amplification and replication properties, of oligonucleotides with the desirable properties of other molecules.

The SELEX method further encompasses combining selected Nucleic Acid Ligands with Lipophilic Compounds or Non-Immunogenic, High Molecular Weight Compounds in a diagnostic or therapeutic Complex as described in U.S. patent application Ser. No. 08/434,465, filed May 4, 1995, entitled "Nucleic Acid Ligand Complexes." Each of the above described patent applications which describe modifications of the basic SELEX procedure are specifically incorporated by reference herein in their entirety.

B. Lipid Constructs

Lipid Bilayer Vesicles are closed, fluid-filled microscopic spheres which are formed principally from individual molecules having polar (hydrophilic) and non-polar (lipophilic) portions. The hydrophilic portions may comprise phosphate, glycerylphosphato, carboxy, sulfato, amino, hydroxy, choline or other polar groups.

Examples of lipophilic groups are saturated or unsaturated hydrocarbons such as alkyl, alkenyl or other lipid groups. Sterols (e.g., cholesterol) and other pharmaceutically acceptable adjuvants (including anti-oxidants like alpha-tocopherol) may also be included to improve vesicle stability or confer other desirable characteristics.

Liposomes are a subset of these bilayer vesicles and are comprised principally of phospholipid molecules that contain two hydrophobic tails consisting of fatty acid chains. Upon exposure to water, these molecules spontaneously align to form spherical, bilayer membranes with the lipophilic ends of the molecules in each layer associated in the center of the membrane and the opposing polar ends forming the respective inner and outer surface of the bilayer membrane(s). Thus, each side of the membrane presents a hydrophilic surface while the interior of the membrane comprises a lipophilic medium. These membranes may be arranged in a series of concentric, spherical membranes separated by thin strata of water, in a manner not dissimilar to the layers of an onion, around an internal aqueous space. These multilamellar vesicles (MLV) can be converted into small or Unilamellar Vesicles (UV), with the application of a shearing force.

The therapeutic use of liposomes includes the delivery of drugs which are normally toxic in the free form. In the liposomal form, the toxic drug is occluded, and may be directed away from the tissues sensitive to the drug and targeted to selected areas. Liposomes can also be used therapeutically to release drugs over a prolonged period of time, reducing the frequency of administration. In addition, liposomes can provide a method for forming aqueous dispersions of hydrophobic or amphiphilic drugs, which are normally unsuitable for intravenous delivery.

In order for many drugs and imaging agents, to have therapeutic or diagnostic potential, it is necessary for them to be delivered to the proper location in the body, and the liposome can thus be readily injected and form the basis for sustained release and drug delivery to specific cell types, or parts of the body. Several techniques can be employed to use liposomes to target encapsulated drugs to selected host tissues, and away from sensitive tissues. These techniques include manipulating the size of the liposomes, their net surface charge, and their route of administration. MLVs, primarily because they are relatively large, are usually rapidly taken up by the reticuloendothelial system (principally the liver and spleen). UVs, on the other hand, have been found to exhibit increased circulation times, decreased clearance rates and greater biodistribution relative to MLVs.

Passive delivery of liposomes involves the use of various routes of administration, e.g., intravenous, subcutaneous, intramuscular and topical. Each route produces differences in localization of the liposomes. Two common methods used to direct liposomes actively to selected target areas involve attachment of either antibodies specific receptor ligands to the surface of the liposomes. Antibodies are known to have a high specificity for their corresponding antigen and have been attached to the surface of liposomes, but the results have been less than successful in many instances. Some efforts, however, have been successful in targeting liposomes to tumors without the use of antibodies, see, for example, U.S. Pat. No. 5,019,369.

An area of development aggressively pursued by researchers is the delivery of agents not only to a specific cell type but into the cell's cytoplasm and, further yet, into the nucleus. This is particularly important for the delivery of biological agents such as DNA, RNA, ribozymes and proteins. A promising therapeutic pursuit in this area involves the use of antisense DNA and RNA oligonucleotides for the treatment of disease. However, one major problem encountered in the effective application of antisense technology is that oligonucleotides in their phosphodiester form are quickly degraded in body fluids and by intracellular and extracellular enzymes, such as endonucleases and exonucleases, before the target cell is reached. Intravenous administration also results in rapid clearance from the bloodstream by the kidney, and uptake is insufficient to produce an effective intracellular drug concentration. Liposome encapsulation protects the oligonucleotides from the degradative enzymes, increases the circulation half-life and increases uptake efficiency as a result of phagocytosis of the Liposomes. In this way, oligonucleotides are able to reach their desired target and to be delivered to cells in vivo.

A few instances have been reported where researchers have attached antisense oligonucleotides to Lipophilic Compounds. Antisense oligonucleotides, however, are only effective as intracellular agents. Antisense oligodeoxyribonucleotides targeted to the epidermal growth factor (EGF) receptor have been encapsulated into Liposomes linked to folate via a polyethylene glycol spacer (folate-PEG-Liposomes) and delivered into cultured KB cells via folate receptor-mediated endocytosis (Wang et al. (1995) Proc. Natl. Acad. Sci. USA 92:3318–3322). In addition, a Lipophilic Compound covalently attached to an antisense oligonucleotide has been demonstrated in the literature (EP 462 145 B1).

C. VEGF

The growth of new blood vessels from existing, endothelium (angiogenesis) is tightly controlled in healthy adults by opposing effects of positive and negative regulators. Under certain pathological conditions, including proliferative retinopathies, rheumatoid arthritis, psoriasis and cancer, positive regulators prevail and angiogenesis contributes to disease progression (reviewed in Folkman (1995) Nature Medicine 1:27–31). In cancer, the notion that angiogenesis represents the rate limiting step of tumor growth and metastasis (Folkman (1971) New Engl. J. Med. 285:1182–1186) is now supported by considerable experimental evidence (reviewed in Aznavoorian et al. (1993) Cancer 71:1368–1383; Fidler and Ellis (1994) Cell 79:185–188; Folkman (1990) J. Nati. Cancer Inst. 82:4–6).

The quantity of blood vessels in tumor tissue is a strong negative prognostic indicator in breast cancer (Weidner et al. (1992) J. Natl. Cancer Inst. 84:1875–1887), prostate cancer (Weidner et al. (1993) Am. J. Pathol. 143:401–409), brain tumors (Li et al.(1994) Lancet 344:82–86), and melanoma (Foss et al. (1996) Cancer Res. 56:2900–2903).

A number of angiogenic growth factors have been described to date among which vascular endothelial growth factor (VEGF) appears to play a key role as a positive regulator of physiological and pathological angiogenesis (reviewed in Brown et al. (1997) Control of Angiogenesis (Goldberg and Rosen, eds.) Birkhauser, Basel, pp. 233–269; Thomas (1996) J. Biol. Chem. 271:603–606). VEGF is a secreted disulfide-linked homodimer that selectively stimulates endothelial cells to proliferate, migrate, and produce matrix-degrading enzymes (Conn et al. (1990) Proc. Natl. Acad. Sci. USA 87:1323–1327); Ferrara and Henzel (1989) Biochem. Biophys. Res. Commun. 161:851–858); Gospodarowicz et al.(1989) Proc. Natl. Acad. Sci. USA 7311–7315); Pepper et al.(1991) Biochem. Biophys. Res. Commun. 181:902–906; Unemori et al. (1992) J. Cell. Physiol. 153:557–562), all of which are processes required for the formation of new vessels. In addition to being the only known endothelial cell specific mitogen, VEGF is unique among angiogenic growth factors in its ability to induce a transient increase in blood vessel permeability to macromolecules (hence its original and alternative name, vascular permeability factor, VPF) (Dvorak et al.(1979) J. Immunol. 122:166–174; Senger et al.(1983) Science 219:983–985; Senger et al.(1986) Cancer Res. 46:5629–5632). Increased vascular permeability and the resulting deposition of plasma proteins in the extravascular space assists the new vessel formation by providing a provisional matrix for the migration of endothelial cells (Dvorak et al.(1995) Am. J. Pathol. 146:1029–1039). Hyperpermeability is indeed a characteristic feature of new vessels, including those associated with tumors (Dvorak et al.(1995) Am. J. Pathol. 146:1029–1039). Furthermore, compensatory angiogenesis induced by tissue hypoxia is now known to be mediated by VEGF (Levy et al.(1996) J. Biol. Chem. 2746–2753; Shweiki et al. (1992) Nature 359:843–845).

VEGF occurs in four forms (VEGF- 121, VEGF- 165, VEGF- 189, VEGF-206) as a result of alternative splicing of the VEGF gene (Houck et al. (1991) Mol. Endocrin. 5:1806–1814; Tischer et al. (1991) J. Biol. Chem. 266:11947–11954). The two smaller forms are diffusable while the larger two forms remain predominantly localized to the cell membrane as a consequence of their high affinity for heparin. VEGF-165 also binds to heparin and is the most abundant form. VEGF-121, the only form that does not bind to heparin, appears to have a lower affinity for the receptors (Gitay-Goren et al. (1996) J. Biol. Chem. 271:5519–5523) as well as lower mitogenic potency (Keyt et al. (1996) J. Biol. Chem. 271:7788–7795). The biological effects of VEGF are mediated by two tyrosine kinase receptors (Flt-1 and Flk-1/KDR) whose expression is highly restricted to cells of endothelial origin (de Vries et al. (1992) Science 255:989–991; Millauer et al. (1993) Cell 72:835–846; Terman et al. (1991) Oncogene 6:519–524). While the expression of both functional receptors is required for high affinity binding, the chemotactic and mitogenic signaling in endothelial cells appears to occur primarily through the KDR receptor (Park et al. (1994) J. Biol. Chem. 269:25646–25654; Seetharam et al. (1995) Oncogene 10:135–147; Waltenberger et al. (1994) J. Biol. Chem. 269:26988–26995). The importance of VEGF and VEGF receptors for the development of blood vessels has recently been demonstrated in mice lacking a single allele for the VEGF gene (Carmeliet et al. (1996) Nature 380:435–439; Ferrara et al. (1996) Nature 380:439–442) or both alleles of the Flt-1 (Fong et al. (1995) 376:66–70) or Flk-1 genes (Shalaby et al. (1995) Nature 376:62–66). In each case, distinct abnormalities in vessel formation were observed resulting in embryonic lethality.

VEGF is produced and secreted in varying amounts by virtually all tumor cells (Brown et al. (1997) Control of Angiogenesis (Goldberg and Rosen, Eds.) Birkhauser, Basel, pp. 233–269). Direct evidence that VEGF and its receptors contribute to tumor growth was recently obtained by a demonstration that the growth of human tumor xenografts in nude mice could be inhibited by neutralizing antibodies to VEGF (Kim et al. (1993) Nature 362:841–844), by the expression of dominant-negative VEGF receptor flk-1 (Millauer et al. (1996) Cancer Res. 56:1615–1620; Millauer et al. (1994) Nature 367:576–579), by low molecular weight inhibitors of Flk-1 tyrosine kinase activity (Strawn et al. (1966) Cancer Res. 56:3540–3545), or by the expression of antisense sequence to VEGF mRNA (Saleh et al. (1996) Cancer Res. 56:393–401). Importantly, the incidence of tumor metastases was also found to be dramatically reduced by VEGF antagonists (Claffey et al. (1996) Cancer Res. 56:172–181).

VEGF inhibitors may have broad clinical utility due to the role of VEGF in a wide variety of diseases including psoriasis, ocular disorders, collagen vascular diseases and neoplastic diseases. Although most tumor types are known to produce VEGF, until recently none has been shown to express functional VEGF receptors. It has been shown that Kaposi's sarcoma (KS) cells not only produce abundant amounts of VEGF but also express functional VEGF receptors and therefore use VEGF for autocrine growth. Kaposi's sarcoma is typically treated with conventional antimetabolic drugs. However, a major shortcoming of the use of chemotherapy in KS patients is the accompanying induction of immunosuppression which has serious consequences in patients whose immune system is already compromised. The need for alternative therapies is especially great in early stages of the disease where KS lesions begin to appear but the patients otherwise feel fairly healthy. In this regard, encapsulation of chemotherapeutic drugs such as daunorubicin into liposomes has recently proved to be a promising method of minimizing side effects of chemotherapy while maintaining anti-tumor efficacy. Drugs with low toxicity that selectively target activated cells of endothelial origin, such as the Nucleic Acid Ligand VEGF antagonists described here, would be an enormous asset in the treatment of KS.

SUMMARY OF THE INVENTION

The present invention provides a method for preparing a Complex comprised of a VEGF Nucleic Acid Ligand and a Lipophilic Compound by the method comprising identifying a Nucleic Acid Ligand from a Candidate Mixture of Nucleic Acids where the Nucleic Acid is a ligand of VEGF by the method of (a) contacting the Candidate Mixture of Nucleic Acids with VEGF, (b) partitioning between members of said Candidate Mixture on the basis of affinity to VEGF, and c) amplifying the selected molecules to yield a mixture of Nucleic Acids enriched for Nucleic Acid sequences with a relatively higher affinity for binding to VEGF, and associating said identified VEGF Nucleic Acid Ligand with a Lipophilic Compound. The invention further comprises a Complex comprised of a VEGF Nucleic Acid Ligand and a Lipophilic Compound. The invention further includes a Lipid Construct comprising a VEGF Nucleic Acid Ligand or a Complex. The present invention further relates to a method for preparing a Complex wherein the Complex is comprised of a VEGF Nucleic Acid Ligand and a Lipophilic Compound associated with a Lipid Construct. In the preferred embodiment, the Lipophilic Compound is dialkylglycerol or diacylglycerol. More preferably, the Lipophilic Compound is 1,2-di-O-octadecyl-sn-glycerol. In the preferred embodiment, the Lipid Construct is a Liposome. In the preferred embodiment, the VEGF Nucleic Acid Ligand is identified by the SELEX method.

In another embodiment, this invention provides a method for improving the pharmacokinetic properties of a VEGF Nucleic Acid Ligand by associating the VEGF Nucleic Acid Ligand with a Lipophilic Compound to form a Complex and administering the Complex to a patient. The invention further relates to improving the pharmacokinetic properties of a VEGF Nucleic Acid Ligand by further associating the Complex with a Lipid Construct.

It is an object of the present invention to provide Complexes comprising one or more VEGF Nucleic Acid Ligands in association with one or more Lipophilic Compounds and methods for producing the same. It is a further object of the present invention to provide Lipid Constructs comprising a Complex. It is a further object of the invention to provide one or more VEGF Nucleic Acid Ligands in association with one or more Lipophilic Compounds with Improved Pharmacokinetic Properties. It is yet a further object of the invention to provide a Lipid Construct comprising one or more Complexes comprising VEGF Nucleic Acid Ligands and one or more Lipophilic Compounds with improved Pharmacokinetic Properties.

In the preferred embodiments of the invention, the Lipid Construct is preferably a Lipid Bilayer Vesicle and most preferably a Liposome. In the preferred embodiments of the invention, the Lipid is a dialkylglycerol or a (diacylglycerol. In the most preferred embodiment, the dialkylglycerol is 1,2-di-O-octadecyl-sn-glycerol. In the preferred embodiment, the VEGF Nucleic Acid Ligand is identified according to the SELEX method.

In embodiments of the invention directed to Complexes comprising a dialkylglycerol or a diacylglycerol in association with a VEGF Nucleic Acid Ligand or ligands, the Nucleic Acid Ligand or Ligands can serve in a targeting capacity.

Additionally, the VEGF Nucleic Acid Ligand can be associated with the Lipid Construct without being part of a Complex.

Furthermore, in embodiments of the invention directed to Lipid Constructs comprising a VEGF Nucleic Acid Ligand or a Complex where the Lipid Construct is of a type that has a membrane defining an interior compartment such as a Lipid Bilayer Vesicle, the VEGF Nucleic Acid Ligand or Complex in association with the Lipid Construct may be associated with the membrane of the Lipid Construct or encapsulated within the compartment. In embodiments where the VEGF Nucleic Acid Ligand is in association with the membrane, the VEGF Nucleic Acid Ligand can associate with the interior-facing or exterior-facing part of the membrane, such that the VEGF Nucleic Acid Ligand is projecting into or out of the vesicle. In embodiments where the Nucleic Acid Ligand is projecting out of the Lipid Construct, the Nucleic Acid Ligand can serve in a targeting capacity.

In embodiments where the VEGF Nucleic Acid Ligand of the Lipid Construct serves in a targeting capacity, the Lipid Construct can have associated with it additional therapeutic or diagnostic agents. In one embodiment, the therapeutic or diagnostic agent is associated with the exterior of the Lipid Construct. In other embodiments, the therapeutic or diagnostic agent is encapsulated in the Lipid Construct or associated with the interior of the Lipid Construct. In yet a further embodiment, the therapeutic or diagnostic agent is associated with the Complex. In one embodiment, the therapeutic agent is a drug. In an alternative embodiment, the therapeutic or diagnostic agent is one or more additional Nucleic Acid Ligands.

It is a further object of the present invention to provide a method for inhibiting angiogenesis by the administration of a Complex or Lipid Construct comprising a VEGF Nucleic Acid Ligand or Complex of the present invention. It is yet a further object of the present invention to provide a method for inhibiting the growth of tumors by the administration of a Complex or Lipid Construct comprising a VEGF Nucleic Acid Ligand or Complex of the present invention. It is yet a further object of the invention to provide a method for inhibiting Kaposi's Sarcoma by the administration of a Complex or Lipid Construct comprising a VEGF Nucleic Acid Ligand or Complex of the present invention.

These and other objects, as well as the nature, scope and utilization of this invention, will become readily apparent to those skilled in the art from the following description and the appended claims.

BRIEF DESCRIPTION OF THE FIGURES

FIGS. 1A–1D show the molecular descriptions of NX278 (SEQ ID NO:2), NX213(SEQ ID NO:1), and scNX278(SEQ ID NO:3), and scNX213(SEQ ID NO:4). A lower case letter preceding a nucleotide indicates the following: m=2'-O-Methyl, a=2'-amino, r=ribo, and f=2'-fluoro. No letter preceding a nucleotide indicates a deoxyribonucleotide (2'H). An S following a nucleotide denotes a backbone modification consisting of a phosphorothioate internucleoside linkage.

DETAILED DESCRIPTION OF THE INVENTION

Definitions

Figure 1B:
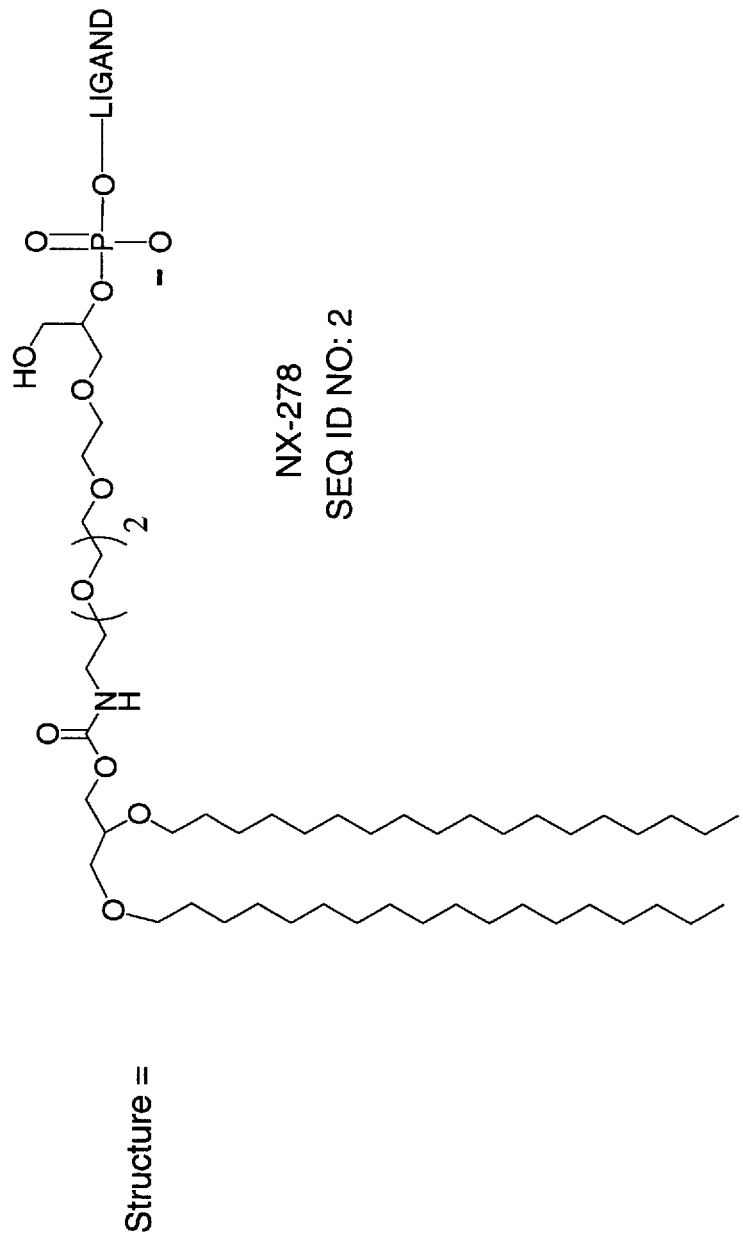

"Covalent Bond" is the chemical bond formed by the sharing of electrons.

"Non-Covalent Interactions" are means by which molecular entities are held together by interactions other than Covalent Bonds including ionic interactions and hydrogen bonds.

"Lipophilic Compounds" are compounds which have the propensity to associate with or partition into lipid and/or other materials or phases with low dielectric constants, including structures that are comprised substantially of lipophilic components. Lipophilic Compounds include lipids as well as non-lipid containing compounds that have the propensity to associate with lipid (and/or other materials or phases with low dielectric constants). Cholesterol, phospholipid, and glycerolipids, such as dialkylglycerol, and diacylglycerol are further examples of Lipophilic Compounds. In one preferred embodiment of the invention, the lipophilic compound bound to the nucleic acid ligand has the structure R—CH$_2$—CHR—CH—, wherein R is independently selected from the group consisting of —O(CH$_2$)$_n$CH$_3$; —(CH$_2$)$_n$CH$_3$; —OC(O)(CH$_2$)$_n$CH$_3$; —S(CH$_2$)$_n$CH$_3$; and —SC(O)(CH$_2$)$_n$CH$_3$, wherein n is 0–30; preferably 10–20.

"Complex" as used herein describes the molecular entity formed by the association of a VEGF Nucleic Acid Ligand with a Lipophilic Compound. The association can be through either Covalent Bonds or Non-Covalent Interactions. In a preferred embodiment of the present invention, the Complex is depicted as A—B—X, wherein A is a lipophilic compound as defined above; B is optional, and may be either a linker Z as described below, or two linkers and a spacer as described below Z—S—Z'; and X is a VEGF nucleic acid ligand.

"Lipid Constructs" for purposes of this invention, are structures containing lipids, phospholipids, or derivatives thereof comprising a variety of different structural arrangements which lipids are known to adopt in aqueous suspension. These structures include, but are not limited to, Lipid Bilayer Vesicles, micelles, Liposomes, emulsions, lipid ribbons or sheets, and may be complexed with a variety of drugs and adjuvants which are known to be pharmaceutically acceptable. In the preferred embodiment, the Lipid Construct is a Liposome. Common adjuvants include cholesterol and alpha-tocopherol, among others. The Lipid Constructs may be used alone or in any combination which one skilled in the art would appreciate to provide the characteristics desired for a particular application. In addition, the technical aspects of Lipid Constructs and Liposome formation are well known in the art and any of the methods commonly practiced in the field may be used for the present invention.

"Nucleic Acid Ligand" as used herein is a non-naturally occurring Nucleic Acid having a desirable action on a SELEX Target. The SELEX Target of the present invention is VEGF, hence the term VEGF Nucleic Acid Ligand. A desirable action includes, but is not limited to, binding of the SELEX Target, catalytically changing the SELEX Target, reacting with the SELEX Target in a way which modifies/alters the SELEX Target or the functional activity of the SELEX Target, covalently attaching to the SELEX Target as in a suicide inhibitor, facilitating the reaction between the Target and another molecule. In the preferred embodiment, the action is specific binding affinity for VEGF, wherein the Nucleic Acid Ligand is not a Nucleic Acid having the known physiological function of being bound by VEGF.

In preferred embodiments of the invention, the VEGF Nucleic Acid Ligand of the Complexes and Lipid Constructs of the invention are identified by the SELEX methodology. VEGF Nucleic Acid Ligands are identified from a Candidate Mixture of Nucleic Acids, said Nucleic Acid being a ligand of VEGF, by the method comprising a) contacting the Candidate Mixture with VEGF, wherein Nucleic Acids having an increased affinity to VEGF relative to the Candidate Mixture may be partitioned from the remainder of the Candidate Mixture; b) partitioning the increased affinity Nucleic Acids from the remainder of the Candidate Mixture; and c) amplifying the increased affinity Nucleic Acids to yield a ligand-enriched mixture of Nucleic Acids (see U.S. patent application Ser. No. 08/233,012, filed Apr. 25, 1994, entitled "High Affinity Oligonucleotides to Vascular Endothelial Growth Factor (VEGF)," U.S. patent application Ser. No. 08/447,169, filed May 19, 1995, entitled "High Affinity Oligonucleotide Ligands to Vascular Endothelial Growth Factor (VEGF)," which are hereby incorporated by reference herein).

"Candidate Mixture" is a mixture of Nucleic Acids of differing sequence from which to select a desired ligand. The source of a Candidate Mixture can be from naturally-occurring Nucleic Acids or fragments thereof, chemically synthesized Nucleic Acids, enzymatically synthesized Nucleic Acids or Nucleic Acids made by a combination of the foregoing techniques. In a preferred embodiment, each Nucleic Acid has fixed sequences surrounding a randomized region to facilitate the amplification process.

"Nucleic Acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the Nucleic Acid Ligand bases or to the Nucleic Acid Ligand as a whole. such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications such as internucleoside phosphorothioate linkages, methylations, unusual base-pairing combinations such as the isobases isocytidine and isoguanidine and the like. Modifications can also include 3' and 5' modifications such as capping.

"Lipid Bilayer Vesicles" are closed, fluid-filled microscopic spheres which are formed principally from individual molecules having polar (hydrophilic) and non-polar (lipophilic) portions. The hydrophilic portions may comprise phosphate, glycerylphosphato, carboxy, sulfato, amino, hydroxy, choline and other polar groups. Examples of non-polar groups are saturated or unsaturated hydrocarbons such as alkyl, alkenyl or other lipid groups. Sterols (e.g., cholesterol) and other pharmaceutically acceptable adjuvants (including anti-oxidants like alpha-tocopherol) may also be included to improve vesicle stability or confer other desirable characteristics.

"Liposomes" are a subset of Lipid Bilayer Vesicles and are comprised principally of phospholipid molecules which contain two hydrophobic tails consisting of long fatty acid chains. Upon exposure to water, these molecules spontaneously align to form a bilayer membrane with the lipophilic ends of the molecules in each layer associated in the center of the membrane and the opposing polar ends forming the respective inner and outer surface of the bilayer membrane. Thus, each side of the membrane presents a hydrophilic surface while the interior of the membrane comprises a lipophilic medium. These membranes when formed are generally arranged in a system of concentric closed membranes separated by interlamellar aqueous phases, in a manner not dissimilar to the layers of an onion, around an internal aqueous space. These multilamellar vesicles (MLV) can be converted into small or unilamellar vesicles (UV), with the application of a shearing force.

"Cationic Liposome" is a Liposome that contains lipid components that have an overall positive charge at physiological pH.

"SELEX" methodology involves the combination of selection of Nucleic Acid Ligands which interact with a SELEX Target in a desirable manner, for example binding to a protein, with amplification of those selected Nucleic Acids. Iterative cycling of the selection/amplification steps allows selection of one or a small number of Nucleic Acids which interact most strongly with the SELEX Target from a pool which contains a very large number of Nucleic Acids. Cycling of the selection/amplification procedure is continued until a selected goal is achieved.

The SELEX methodology is described in the SELEX Patent Applications.

"SELEX Target" means any compound or molecule of interest for which a ligand is desired. A Target can be a protein (such as VEGF, thrombin, and selectin), peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. The terms "SELEX Target" and "Target" can be used interchangeably herein. It will be clear from the sentence context whether or not "Target" means "SELEX Target." The principal SELEX Target of the subject invention is VEGF.

"Target" means a preselected location in a biological system including tissues, organs, cells, intracellular compartments, extracellular components. The latter include hormones (endocrine paracrine, autocrine), enzymes, neurotransmitters and constituents of physiological cascade phenomena (e.g., blood coagulation, complement, etc.).

"Improved Pharmacokinetic Properties" means that the VEGF Nucleic Acid Ligand in association with the Lipophilic Compound and/or Lipid Construct shows a longer circulation half-life in vivo relative to the same VEGF Nucleic Acid Ligand not in association with a Lipophilic Compound and/or Lipid Construct.

"Linker" is a molecular entity that connects two or more molecular entities through Covalent Bond or Non-Covalent Interactions.

"Spacer" is a Linker of the size that allows spatial separation of two or more molecular entities in a manner that preserves the functional properties of one or more of the molecular entities.

"Therapeutic" as used herein, includes treatment and/or prophylaxis. When used, Therapeutic refers to humans and other animals.

It is an object of the present invention to provide Complexes comprising one or more VEGF Nucleic Acid Ligands in association with a Lipophilic Compound. Such Complexes have one or more of the following advantages over a VEGF Nucleic Acid Ligand not in association with a Lipophilic Compound: 1) Improved Pharmacokinetic Properties, 2) improved capacity for intracellular delivery, or 3) improved capacity for targeting. It is a further object of the present invention to provide Lipid Constructs comprising a VEGF Nucleic Acid Ligand or a Complex comprised of a VEGF Nucleic Acid Ligand in association with a Lipophilic Compound. The Lipid Constructs have the same advantages.

The Complexes or the Lipid Constructs comprising the VEGF Nucleic Acid Ligand or Complexes may benefit from one, two, or three of these advantages. For example, a Lipid Construct of the present invention may be comprised of a) a Liposome, b) a drug that is encapsulated within the interior of the Liposome, and c) a Complex comprised of a VEGF Nucleic Acid Ligand and Lipophilic Compound, wherein the VEGF Nucleic Acid Ligand component of the Complex is associated with and projecting from the exterior of the Lipid Construct. In such a case, the Lipid Construct comprising a Complex will 1) have Improved Pharmacokinetic Properties due to the presence of the Liposome, 2) have enhanced capacity for intracellular delivery of the encapsulated drug due to the properties of the Liposome, and 3) be specifically targeted to the preselected location in vivo that is expressing VEGF by the exteriorly associated VEGF Nucleic Acid Ligand.

In another embodiment, the Complex of the present invention is comprised of a VEGF Nucleic Acid Ligand covalently attached to a Lipophilic Compound such as dialkylglycerol or diacylglycerol. In this case, the pharmacokinetic properties of the Complex will be enhanced relative to the VEGF Nucleic Acid Ligand alone. In another embodiment, the pharmacokinetic properties of the VEGF Nucleic Acid Ligand is enhanced relative to the VEGF Nucleic Acid Ligand alone when the VEGF Nucleic Acid Ligand is covalently attached to a Lipophilic Compound and is further associated with a Lipid Construct or the VEGF Nucleic Acid Ligand is encapsulated within a Lipid Construct.

In embodiments where there are multiple VEGF Nucleic Acid Ligands, there is an increase in avidity due to multiple binding interactions with VEGF. Furthermore, in embodiments where the Complex is comprised of multiple VEGF Nucleic Acid Ligands, the pharmacokinetic properties of the Complex will be improved relative to one VEGF Nucleic Acid Ligand alone. In embodiments where a Lipid Construct comprises multiple Nucleic Acid Ligands or Complexes, the Pharmacokinetic Properties of the VEGF Nucleic Acid Ligand will be improved relative to Lipid Constructs in which there is only one Nucleic Acid Ligand or Complex.

The Lipophilic Compound can be covalently bonded or associated through Non-Covalent Interactions with the VEGF Nucleic Acid Ligand(s). In embodiments where the Lipophilic Compound is dialkylglycerol or diacylglycerol, a covalent association with the VEGF Nucleic Acid Ligand(s) is preferred. In embodiments where covalent attachment is employed, the Lipophilic Compound may be covalently bound to a variety of positions on the VEGF Nucleic Acid Ligand, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the VEGF Nucleic Acid Ligand. Preferably, however, it is bonded to the 5' or 3' hydroxyl of the phosphate group thereof. Attachment of the VEGF Nucleic Acid Ligand to other components of the Complex can be done directly or with the utilization of Linkers or Spacers. In embodiments where the Lipid Construct comprises a Complex, or where the VEGF Nucleic Acid Ligands are encapsulated within the Liposome, a non-covalent association between the VEGF Nucleic Acid Ligand or the Complex and the Lipid Construct is preferred.

One problem encountered in the therapeutic use of Nucleic Acids is that oligonucleotides in their phosphodiester form may be quickly degraded in body fluids by intracellular and extracellular enzymes such as endonucleases and exonucleases before the desired effect is manifest. Certain chemical modifications of the VEGF Nucleic Acid Ligand can be made to increase the in vivo stability of the VEGF Nucleic Acid Ligand or to enhance or to mediate the delivery of the VEGF Nucleic Acid Ligand. Modifications of the VEGF Nucleic Acid Ligands contemplated in this invention include, but are not limited to, those which provide other chemical groups that incorporate additional charge, polarizability, hydrophobicity, hydrogen bonding, electrostatic interaction, and fluxionality to the VEGF Nucleic Acid Ligand bases or to the VEGF Nucleic Acid Ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping.

Where the Nucleic Acid Ligands are derived by the SELEX method, the modifications can be pre- or post-SELEX modifications. Pre-SELEX modifications yield VEGF Nucleic Acid Ligands with both specificity for VEGF and improved in vivo stability. Post-SELEX modifications made to 2'-OH Nucleic Acid Ligands can result in improved in vivo stability without adversely affecting the binding capacity of the Nucleic Acid Ligands. The preferred modifications of the VEGF Nucleic Acid Ligands of the subject invention are 5' and 3' phosphorothioate capping or 3'3' inverted phosphodiester linkage at the 3' end. For RNA ligands, additional 2' amino ($2'-NH_2$) and 2' O methyl (2'OMe) modification of some or all of the nucleotides is preferred.

In another aspect of the present invention, the association of the VEGF Nucleic Acid Ligand with a Lipophilic Compound results in Improved Pharmacokinetic Properties (i.e., slower clearance rate) relative to the VEGF Nucleic Acid Ligand not in association with a Lipophilic Compound. The Complex with the VEGF Nucleic Acid Ligand can be formed through covalent or Non-Covalent Interactions. In another aspect of the present invention, the association of a VEGF Nucleic Acid Ligand or a Complex comprised of a VEGF Nucleic Acid Ligand with a Lipophilic Compound with a Lipid Construct results in Improved Pharmacokinetic Properties relative to the VEGF Nucleic Acid Ligand or Complex not in association with a Lipid Construct. The VEGF Nucleic Acid Ligand or Complex can be associated with the Lipid Construct through covalent or Non-Covalent Interactions. In another aspect, the VEGF Nucleic Acid Ligand can be associated with the Lipid Construct through covalent or Non-Covalent Interactions. In a preferred embodiment, the association is through Non-Covalent Interactions. In a preferred embodiment, the Lipid Construct is a Lipid Bilayer Vesicle. In the most preferred embodiment, the Lipid Construct is a Liposome.

Liposomes for use in the present invention can be prepared by any of the various techniques presently known in the art or subsequently developed. Typically, they are prepared from a phospholipid, for example, distearoyl phosphatidylcholine, and may include other materials such as neutral lipids, for example, cholesterol, and also surface modifiers such as positively charged (e.g., sterylimine or aminomannose or aminomannitol derivatives of cholesterol) or negatively charged (e.g., diacetyl phosphate, phosphatidyl glycerol) compounds. Multilamellar Liposomes can be formed by conventional techniques, that is, by depositing a selected lipid on the inside wall of a suitable container or vessel by dissolving the lipid in an appropriate solvent, and then evaporating the solvent to leave a thin film on the inside of the vessel or by spray drying. An aqueous phase is then added to the vessel with a swirling or vortexing motion which results in the formation of MLVs. UVs can then be formed by homogenization, sonication or extrusion (through filters) of MLV's. In addition, UVs can be formed by detergent removal techniques.

In certain embodiments of this invention, the Lipid Construct comprises a targeting VEGF Nucleic Acid Ligand(s) associated with the surface of the Lipid Construct and an encapsulated therapeutic or diagnostic agent. Preferably the Lipid Construct is a Liposome. Preformed Liposomes can be modified to associate with the VEGF Nucleic Acid Ligands. For example, a Cationic Liposome associates through electrostatic interactions with the VEGF Nucleic Acid Ligand. Alternatively, a VEGF Nucleic Acid Ligand attached to a Lipophilic Compound, such as dialkylglycerol, can be added to preformed Liposomes whereby the dialkylglycerol becomes associated with the Liposomal membrane. Alternatively, the VEGF Nucleic Acid Ligand can be associated with the Liposome during the formulation of the Liposome. Preferably, the VEGF Nucleic Acid Ligand is associated with the Liposome by loading into preformed Liposomes.

It is well known in the art that Liposomes are advantageous for encapsulating or incorporating a wide variety of therapeutic and diagnostic agents. Any variety of compounds can be enclosed in the internal aqueous compartment of the Liposomes. Illustrative therapeutic agents include antibiotics, antiviral nucleosides, antifungal nucleosides, metabolic regulators, immune modulators, chemotherapeutic drugs, toxin antidotes, DNA, RNA, antisense oligonucleotides, Nucleic Acid Ligands, etc. By the same token, the Lipid Bilayer Vesicles may be loaded with a diagnostic radionuclide (e.g., Indium 111, Iodine 131, Yttrium 90, Phosphorous 32, or gadolinium) and fluorescent materials or other materials that are detectable in in vitro and in vivo applications. It is to be understood that the therapeutic or diagnostic agent can be encapsulated by the Liposome walls in the aqueous interior. Alternatively, the carried agent can be a part of, that is, dispersed or dissolved in the vesicle wall-forming materials.

During Liposome formation, water soluble carrier agents may be encapsulated in the aqueous interior by including them in the hydrating solution, and lipophilic molecules incorporated into the lipid bilayer by inclusion in the lipid formulation. In the case of certain molecules (e.g., cationic or anionic lipophilic drugs), loading of the drug into preformed Liposomes may be accomplished, for example, by the methods described in U.S. Pat. No. 4,946,683, the disclosure of which is incorporated herein by reference. Following drug encapsulation, the Liposomes are processed to remove unencapsulated drug through processes such as gel chromatography or ultrafiltration. The Liposomes are then typically sterile filtered to remove any microorganisms which may be present in the suspension. Microorganisms may also be removed through aseptic processing.

If one wishes to encapsulate large hydrophilic molecules with Liposomes, larger unilamellar vesicles can be formed by methods such as the reverse-phase evaporation (REV) or solvent infusion methods. Other standard methods for the formation of Liposomes are known in the art, for example, methods for the commercial production of Liposomes include the homogenization procedure described in U.S. Pat. No. 4,753,788 and the thin-film evaporation method described in, U.S. Pat. No. 4,935,171, which are incorporated herein by reference.

It is to be understood that the therapeutic or diagnostic agent can also be associated with the surface of the Lipid Bilayer Vesicle. For example, a drug can be attached to a phospholipid or glyceride (a prodrug). The phospholipid or glyceride portion of the prodrug can be incorporated into the lipid bilayer of the Liposome by inclusion in the lipid formulation or loading into preformed Liposomes (see U.S. Pat. Nos. 5,194,654 and 5,223,263, which are incorporated by reference herein).

It is readily apparent to one skilled in the art that the particular Liposome preparation method will depend on the intended use and the type of lipids used to form the bilayer membrane.

The efficiency of delivery of the VEGF Nucleic Acid Ligand to cells may be optimized by using lipid formulations and conditions known to enhance fusion of Liposomes with cellular membranes. For example, certain negatively charged lipids such as phosphatidylglycerol and phosphatidylserine promote fusion, especially in the presence of other fusogens (e.g., multivalent cations like Ca2+, free fatty acids, viral fusion proteins, short chain PEG, lysolecithin, detergents and surfactants). Phosphatidylethanolamine may also be included in the Liposome formulation to increase membrane fusion and, concomitantly, enhance cellular delivery. In addition, free fatty acids and derivatives thereof, containing, for example, carboxylate moieties, may be used to prepare pH-sensitive Liposomes which are negatively charged at higher pH and neutral or protonated at lower pH. Such pH-sensitive Liposomes are known to possess a greater tendency to fuse.

In the preferred embodiment, the VEGF Nucleic Acid Ligands of the present invention are derived from the SELEX methodology. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, now U.S. Pat. No. 5,475,096, U.S. patent application Ser. No. 07/931, 473, filed Aug. 17, 1992, entitled Methods for Identifying Nucleic Acid Ligands, now U.S. Pat. No. 5,270,163 (see also WO 91/19813). These applications, each specifically incorporated herein by reference, are collectively called the SELEX Patent Applications.

The SELEX process provides a class of products which are Nucleic Acid molecules, each having a unique sequence, and each of which has the property of binding specifically to a desired Target compound or molecule. Target molecules are preferably proteins, but can also include among others carbohydrates, peptidoglycans and a variety of small molecules. SELEX methodology can also be used to Target biological structures, such as cell surfaces or viruses, through specific interaction with a molecule that is an integral part of that biological structure.

In its most basic form, the SELEX process may be defined by the following series of steps:

1) A Candidate Mixture of Nucleic Acids of differing sequence is prepared. The Candidate Mixture generally includes regions of fixed sequences (i.e., each of the members of the Candidate Mixture contains the same sequences in the same location) and regions of randomized sequences. The fixed sequence regions are selected either: (a) to assist in the amplification steps described below, (b) to mimic a sequence known to bind to the Target, or (c) to enhance the concentration of a given structural arrangement of the Nucleic Acids in the Candidate Mixture. The randomized sequences can be totally randomized (i.e., the probability of finding a base at any position being one in four) or only partially randomized (e.g., the probability of finding a base at any location can be selected at any level between 0 and 100 percent).

2) The Candidate Mixture is contacted with the selected Target under conditions favorable for binding between the Target and members of the Candidate Mixture. Under these circumstances, the interaction between the Target and the Nucleic Acids of the Candidate Mixture can be considered as forming Nucleic Acid-target pairs between the Target and those Nucleic Acids having the strongest affinity for the Target.

3) The Nucleic Acids with the highest affinity for the target are partitioned from those Nucleic Acids with lesser affinity to the target. Because only an extremely small number of sequences (and possibly only one molecule of Nucleic Acid) corresponding to the highest affinity Nucleic Acids exist in the Candidate Mixture, it is generally desirable to set the partitioning criteria so that a significant amount of the Nucleic Acids in the Candidate Mixture (approximately 5–50%) are retained during partitioning.

4) Those Nucleic Acids selected during partitioning as having the relatively higher affinity for the target are then amplified to create a new Candidate Mixture that is enriched in Nucleic Acids having a relatively higher affinity for the target.

5) By repeating the partitioning and amplifying steps above, the newly formed Candidate Mixture contains fewer and fewer unique sequences, and the average degree of affinity of the Nucleic Acids to the target will generally increase. Taken to its extreme, the SELEX process will yield a Candidate Mixture containing one or a small number of unique Nucleic Acids representing those Nucleic Acids from the original Candidate Mixture having the highest affinity to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure", describes the use of SELEX in conjunction with gel electrophoresis to select Nucleic Acid molecules with specific structural characteristics, such as bent DNA. U.S. patent application Ser. No. 08/123,935, filed Sep. 17, 1993, entitled "Photoselection of Nucleic Acid Ligands" describes a SELEX based method for selecting Nucleic Acid Ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," abandoned in favor of U.S. patent application Ser. No. 08/443, 957, now U.S. Pat. No. 5,580,737, describes a method for identifying highly specific Nucleic Acid Ligands able to discriminate between closely related molecules, termed Counter-SELEX. U.S. patent application Ser. No. 08/143, 564, filed Oct. 25, 1993, entitled "Systematic Evolution of Ligands by EXponential Enrichment: Solution SELEX," abandoned in favor of U.S. patent application Ser. No. 08/143,564, now U.S. Pat. No. 5,546,938, describes a SELEX-based method which achieves highly efficient partitioning between oligonucleotides having high and low affinity for a target molecule. U.S. patent application Ser. No. 07/964,624, filed Oct. 21, 1992, entitled "Nucleic Acid Ligands" to HIV-RT and HIV-1 Rev, now U.S. Pat. No. 5,496,938, describes methods for obtaining improved Nucleic Acid Ligands after SELEX has been performed. U.S. patent application Ser. No. 08/400,440, filed Mar. 8, 1995, entitled "Systematic Evolution of Ligands by EXponential Enrichment: Chemi-SELEX", now U.S. Pat. No. 5,705,337, describes methods for covalently linking a ligand to its target.

The SELEX method encompasses the identification of high-affinity Nucleic Acid Ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified Nucleic Acid Ligands containing modified nucleotides are described in U.S. patent application Ser. No. 08/117,991, filed Sep. 8, 1993, entitled "High Affinity Nucleic Acid Ligands Containing Modified Nucleotides," abandoned in favor of U.S. patent application Ser. No. 08/430,709, now U.S. Pat. No. 5,660,985, that describes oligonucleotides containing nucleotide derivatives chemically modified at the 5- and 2'-positions of pyrimidines. U.S. patent application Ser. No. 08/134,028, supra, describes highly specific Nucleic Acid Ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2'-Modified Nucleosides by Intramolecular Nucleophilic Displacement", describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX," now U.S. Pat. No. 5,637, 459, and U.S. patent application Ser. No. 08/234,997, filed Apr. 28, 1994, entitled "Systematic Evolution of Ligands by Exponential Enrichment: Blended SELEX," now U.S. Pat. No. 5,683,867, respectively. These applications allow the combination of the broad array of shapes and other properties, and the efficient amplification and replication properties, of oligonucleotides with the desirable properties of other molecules.

The SELEX method further encompasses combining selected Nucleic Acid Ligands with Lipophilic Compounds or Non-Immunogenic, High Molecular Weight Compounds in a diagnostic or therapeutic Complex as described in U.S. patent application Ser. No. 08/434,465, filed May 4, 1995, entitled "Nucleic Acid Ligand Complexes." Each of the above described patent applications which describe modifications of the basic SELEX procedure are specifically incorporated by reference herein in their entirety.

SELEX identifies Nucleic Acid Ligands that are able to bind targets with high affinity and with outstanding specificity, which represents a singular achievement that is unprecedented in the field of Nucleic Acids research. These characteristics are, of course, the desired properties one skilled in the art would seek in a therapeutic or diagnostic ligand.

In order to produce Nucleic Acid Ligands desirable for use as a pharmaceutical, it is preferred that the Nucleic Acid Ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the Nucleic Acid Ligand has the highest possible affinity to the target. Additionally, Nucleic Acid Ligands can have facilitating properties.

In co-pending and commonly assigned U.S. patent application Ser. No. 07/964,624, filed Oct. 21, 1992 ('624), now U.S. Pat. No. 5,496,938, methods are described for obtaining improved Nucleic Acid Ligands after SELEX has been performed. The '624 application, entitled Nucleic Acid Ligands to HIV-RT and HIV-1 Rev, is specifically incorporated herein by reference.

The SELEX process has been used to identify a group of high affinity Nucleic Acid Ligands to VEGF from random 2'-aminopyrimidine RNA libraries (U.S. patent application Ser. No. 08/447,169, filed May 19, 1995, entitled High-Affinity Oligonucleotide Ligands to Vascular Endothelial Growth Factor (VEGF), which is a Continuation-in-Part Application of U.S. patent application Ser. No. 08/233,012, filed Apr. 25, 1994, entitled High-Affinity Oligonucleotide Ligands to Vascular Endothelial Growth Factor (VEGF) both of which are incorporated herein by reference; see also Green et al. (1995) Chemistry and Biology 2:683–695.

In a preferred VEGF Nucleic Acid Ligand (NX213; SEQ ID NO: 1) (See FIG. 1A for molecular description), the subnanomolar binding affinity to VEGF was encoded in a sequence of 24 nucleotides. Additional resistance to nuclease degradation was achieved by adding short phosphorothioate caps at both termini and by substituting 10 out of 14 ribopurine nucleotides at permissive positions by 2'-O-methylpurine nucleotides. The subject invention relates to the Complexing of VEGF Nucleic Acid Ligands with Lipophilic Compounds. The invention further relates to Lipid Constructs comprising a VEGF Nucleic Acid Ligand or a Complex comprised of a VEGF Nucleic Acid Ligand and a Lipophilic Compound. In the examples below, NX213 is used to demonstrate the Complexing with Lipophilic Compounds and associating the Complex with a Lipid Construct.

In embodiments where the VEGF Nucleic Acid Ligand(s) can serve in a targeting capacity, the VEGF Nucleic Acid Ligands adopt a three dimensional structure that must be retained in order for the VEGF Nucleic Acid Ligand to be able to bind its target. In embodiments where the Complex is associated with a Lipid Construct and the VEGF Nucleic Acid Ligand is projecting from the surface of the Lipid Construct, the VEGF Nucleic Acid Ligand must be properly oriented with respect to the surface of the Lipid Construct so that its target binding capacity is not compromised. This can be accomplished by attaching the VEGF Nucleic Acid Ligand at a position that is distant from the binding portion of the VEGF Nucleic Acid Ligand. The three dimensional structure and proper orientation can also be preserved by use of a Linker or Spacer as described supra.

Any variety of therapeutic or diagnostic agents can be attached to the Complex for targeted delivery by the Complex. In addition, any variety of therapeutic or diagnostic agents can be attached, encapsulated, or incorporated into the Lipid Construct as discussed supra for targeted delivery by the Lipid Construct. In embodiments where the Complex is comprised of lipid and VEGF Nucleic Acid Ligand in association with a Liposome, for example, the VEGF Nucleic Acid Ligand could target tumor cells expressing VEGF (e.g., in Kaposi's sarcoma) for delivery of an antitumor drug (e.g., daunorubicin) or imaging agent (e.g., radiolabels). It should be noted that cells and tissues surrounding the tumor may also express VEGF, and targeted delivery of an antitumor drug to these cells would also be effective.

It is further contemplated by this invention that the agent to be delivered can be incorporated into the Complex in such a way as to be associated with the outside surface of the Liposome (e.g., a prodrug, receptor antagonist, or radioactive substance for treatment or imaging). As with the VEGF Nucleic Acid Ligand, the agent can be associated through covalent or Non-Covalent Interactions. The Liposome would provide targeted delivery of the agent extracellularly, with the Liposome serving as a Linker.

In an alternative embodiment of the present invention, VEGF Nucleic Acid Ligands and a Nucleic Acid Ligand to a different SELEX Target can be attached to the surface of the same Liposome. This provides the possibility of bringing VEGF in close proximity to a different SELEX Target and can be used to generate specific interactions between VEGF and the other SELEX Target.

The Lipid Construct comprising a Complex allows for the possibility of multiple binding interactions with VEGF. This, of course, depends on the number of VEGF Nucleic Acid Ligands per Complex and the number of Complexes per Lipid Construct, and the mobility of the VEGF Nucleic Acid Ligands and receptors in their respective membranes. Since the effective binding constant may increase as the product of the binding constant for each site, there is a substantial advantage to having multiple binding interactions. In other words, by having many VEGF Nucleic Acid Ligands attached to the Lipid Construct, and therefore creating multivalency, the effective affinity (i.e., the avidity) of the multimeric Complex for VEGF may become as good as the product of the binding constant for each site.

In certain embodiments of the invention, the Complex of the present invention is comprised of a Nucleic Acid Ligand attached to a Lipophilic Compound such as dialkylglycerol or diacylglycerol. In this case, the pharmacokinetic properties of the Complex will be improved relative to the VEGF Nucleic Acid Ligand alone. As discussed supra, diacylglycerol or dialkylglycerol may be covalently bound to the VEGF Nucleic Acid Ligand at numerous positions on the VEGF Nucleic Acid Ligand. In embodiments where diacylglycerol is used, it is preferred that the VEGF Nucleic Acid Ligand is bonded to the lipid via an amide linkage. In embodiments where dialkylglycerol is used, it is preferred that the VEGF Nucleic Acid Ligand is bonded to the lipid via a phosphodiester linkage.

In another embodiment of the invention, the Lipid Construct comprises a VEGF Nucleic Acid Ligand or Complex. In the preferred embodiment the Lipid Construct is a Liposome. In this embodiment, the dialkylglycerol or diacylglycerol can assist in the incorporation of the VEGF Nucleic Acid Ligand into the Liposome due to the propensity for dialkylglycerol or diacylglycerol to associate with other Lipophilic Compounds. The dialkylglycerol or diacylglycerol in association with a VEGF Nucleic Acid Ligand can be incorporated into the lipid bilayer of the Liposome by inclusion in the formulation or by loading into preformed Liposomes. In the preferred embodiment, the dialkylglycerol or diacylglycerol/VEGF Nucleic Acid Ligand Complex is associated with a preformed Liposome.

It is to be understood that additional compounds can be associated with the Lipid Complex to further improve the Pharmacokinetic Properties of the Lipid Complex. For example, polyethylene glycol may be attached to the exterior-facing part of the membrane of the Lipid Complex.

VEGF Nucleic Acid Ligands selectively bind VEGF. Thus, a Complex comprising VEGF Nucleic Acid Ligand and a Lipophilic Compound, a Lipid Construct comprising a VEGF Nucleic Acid Ligand or a Complex comprised of a VEGF Nucleic Acid Ligand and a Lipophilic Compound are useful as pharmaceuticals or diagnostic agents. The present invention, therefore, includes methods of inhibiting angiogenesis by administration of a Complex comprising VEGF Nucleic Acid Ligand and a Lipophilic Compound, a Lipid Construct comprising a VEGF Nucleic Acid Ligand or a Complex comprised of a VEGF Nucleic Acid Ligand and a Lipophilic Compound. The VEGF Nucleic Acid Ligand-containing Complexes and Lipid Constructs can be used to treat, inhibit, prevent or diagnose any disease state that involves inappropriate VEGF production, particularly angiogenesis. Angiogenesis rarely occurs in healthy adults, except during the menstrual cycle and wound healing. Angiogenesis is a central feature, however, of various disease states, including, but not limited to cancer, diabetic retinopathy, psoriasis and rheumatoid arthritis. The present invention, thus, also includes, but is not limited to, methods of treating, inhibiting, preventing or diagnosing diabetic retinopathy, psoriasis and rheumatoid arthritis. Additionally, VEGF is produced and secreted in varying amounts by virtually all tumor cells. Thus, the present invention, includes methods of treating, inhibiting, preventing, or diagnosing cancer by administration of a Complex comprising VEGF Nucleic Acid Ligand and a Lipophilic Compound, a Lipid Construct comprising a Complex comprised of a VEGF Nucleic Acid Ligand and a Lipophilic Compound, or a VEGF Nucleic Acid Ligand in association with a Lipid Construct without being part of a Complex. It has been shown that in a type of cancer, Kaposi's sarcoma (KS), cells not only produce abundant amounts of VEGF but also express functional VEGF receptors and therefore use VEGF for autocrine growth. Thus, the present invention, includes method of inhibiting Kaposi's Sarcoma by administration of a Complex comprising VEGF Nucleic Acid Ligand and a Lipophilic Compound, a Lipid Construct comprising a Complex comprised of a VEGF Nucleic Acid Ligand and a Lipophilic Compound, or a VEGF Nucleic Acid Ligand in association with a Lipid Construct without being part of a Complex.

In one embodiment of the present invention, the Lipid Construct comprises a Complex comprised of a VEGF Nucleic Acid Ligand and a Lipophilic Compound with an additional diagnostic or therapeutic agent encapsulated in the Lipid Construct or associated with the interior of the Lipid Construct. In the preferred embodiment, the Lipid Construct is a Lipid Bilayer Vesicle, and more preferably a Liposome. The therapeutic use of Liposomes includes the delivery of drugs which are normally toxic in the free form. In the liposomal form, the toxic drug is occluded, and may be directed away from the tissues sensitive to the drug and targeted to selected areas. Liposomes can also be used therapeutically to release drugs over a prolonged period of time, reducing the frequency of administration. In addition, liposomes can provide a method for forming aqueous dispersions of hydrophobic or amphiphilic drugs, which are normally unsuitable for intravenous delivery.

In order for many drugs and imaging agents to have therapeutic or diagnostic potential, it is necessary for them to be delivered to the proper location in the body, and the liposome can thus be readily injected and form the basis for sustained release and drug delivery to specific cell types, or parts of the body. Several techniques can be employed to use liposomes to target encapsulated drugs to selected host tissues, and away from sensitive tissues. These techniques include manipulating the size of the liposomes, their net surface charge, and their route of administration. MLVs, primarily because they are relatively large, are usually rapidly taken up by the reticuloendothelial system (principally the liver and spleen). UVs, on the other hand, have been found to exhibit increased circulation times, decreased clearance rates and greater biodistribution relative to MLVs.

Passive delivery of liposomes involves the use of various routes of administration, e.g., intravenous, subcutaneous, intramuscular and topical. Each route produces differences in localization of the liposomes. Two common methods used to direct liposomes actively to selected target areas involve attachment of either antibodies or specific receptor ligands to the surface of the liposomes. In one embodiment of the present invention, the VEGF Nucleic Acid Ligand is associated with the outside surface of the liposome, and serves in a targeting capacity. Additional targeting components, such as antibodies or specific receptor ligands can be included on the liposome surface, as would be known to one of skill in the art. In addition, some efforts have been successful in targeting liposomes to tumors without the use of antibodies, see, for example, U.S. Pat. No. 5,019,369, U.S. Pat. No. 5,435,989, and U.S. Pat. No. 4,441,775, and it would be known to one of skill in the art to incorporate these alternative targeting methods.

Therapeutic or diagnostic compositions of a Complex comprising VEGF Nucleic Acid Ligand and a Lipophilic Compound, a Lipid Construct comprising a Complex comprised of a VEGF Nucleic Acid Ligand and a Lipophilic Compound, and a VEGF Nucleic Acid Ligand in association with a Lipid Construct without being part of a Complex may be administered parenterally by injection, although other effective administration forms, such as intraarticular injection, inhalant mists, orally active formulations, transdermal iotophoresis or suppositories, are also envisioned. One preferred carrier is physiological saline solution, but it is contemplated that other pharmaceutically acceptable carriers may also be used. In one embodiment, it is envisioned that the carrier and the VEGF Nucleic Acid Ligand Complex constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the VEGF Nucleic Acid ligand. Such excipients are those substances usually and customarily employed to formulate dosages for parental administration in either unit dose or multi-dose form.

Once the therapeutic or diagnostic composition has been formulated, it may be stored in sterile vials as a solution, suspension, gel, emulsion, solid, or dehydrated or lyophilized powder. Such formulations may be stored either in ready to use form or requiring reconstitution immediately prior to administration. The manner of administering formulations containing VEGF Nucleic Acid Ligand for systemic delivery may be via subcutaneous, intramuscular, intravenous, intranasal or vaginal or rectal suppository.

The following examples are provided to explain and illustrate the present invention and are not to be taken as limiting of the invention. The structures of the Nucleic Acid Ligands described in the examples below are shown in FIG. 1. Example 1 describes the conjugation of Nucleic Acid Ligands with lipid reagents. The ability of a dialkylglycerol derivative of the VEGF Nucleic Acid Ligand (NX278; SEQ ID NO: 2)), either as a free ligand or incorporated in the bilayer of liposomes (NX278-L), to inhibit the activity of VEGF in vitro and in vivo is described in Example 2.

EXAMPLE 1

Synthesis of a dialkyl glycerol (1,2-di-O-octadecyl-sn-glycerol)—modified VEGF Nucleic Acid Ligand In this example, conjugation of Nucleic Acid Ligands with lipid reagents is described. Synthesis of (1,2-di-O-octadecyl-sn-glycerol)—modified VEGF Nucleic Acid Ligand is shown below.

Scheme 1

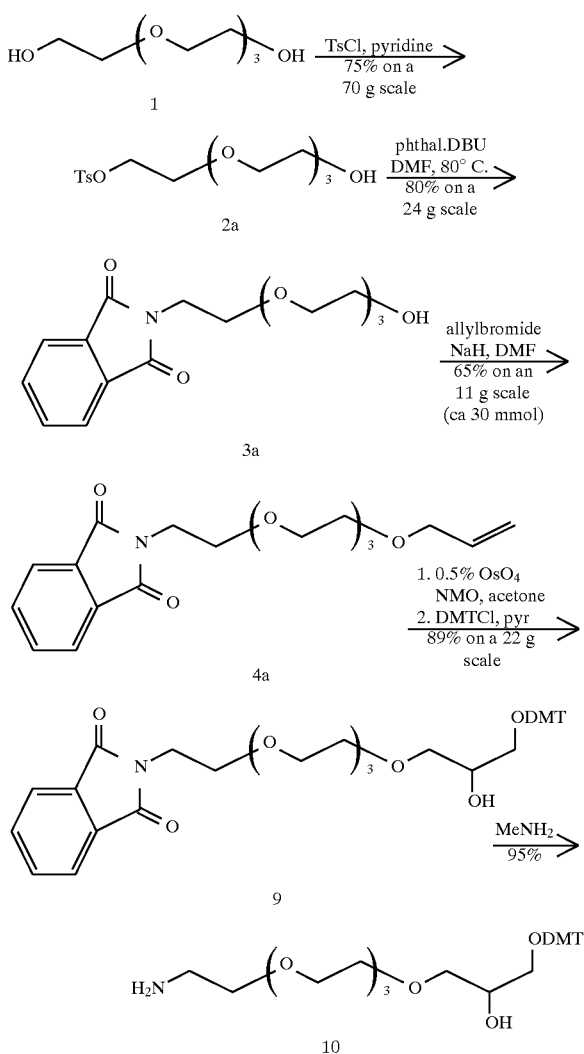

Tetraethylene glycol monotosylate (2a): Tetraethylene glycol (200 mL, 1.15 mol) was dissolved in 500 mL of pyridine and cooled to 0° C. and treated with 22.0 g (0.115 mol) of p-toluenesulfonyl chloride. When solution was complete, the reaction mixture was stored in the refrigerator overnight., and then concentrated in vacuo. The residue was dissolved in 800 mL of EtOAc and extracted with 3×600 mL of H$_2$O. The H$_2$O fractions were back-extracted with EtOAc, and the combined EtOAc fractions were extracted with saturated aqueous Na$_2$HPO$_4$. The organic phase was dried over MgSO$_4$ and concentrated to a colorless oil The oil was purified by flash chromatography using 800 mL of silica gel and eluting with hexane, 25% EtOAc-50% EtOAc in hexane, then EtOAc, then 10% MeOH-20% MeOH in EtOAc to afford 23.7 g (60%) of pure product and 11% of product containing a minor impurity. 2a: $^1$H NMR (300 MHz, CDCl$_3$) d 7.77 (d, J=8.1 Hz, 2H), 7.32 (d, J=8.1 Hz, 2H), 4.13 (t, J=4.8 Hz, 2H), 3.68–3.53 (m, 14H), 2.58 (t, J=5.6 Hz, 1H), 2.42 (s, 3H); $^{13}$C NMR (75 MHz, CDCl$_3$) d 168.2, 158.3, 144.8, 135.9, 133.8, 132.0, 129.9, 128.0, 127.7, 126.6, 123.1, 113.0, 85.9, 73.0, 70.6, 70.4, 70.0, 69.7, 67.8, 64.4, 55.1, 37.1; Low resolution MS m/e calculated for C$_{15}$H$_{24}$O$_8$S (M+1): 349.1.

Tetraethylene glycol monophthalimide (3a): To a stirred solution of 31.96 g (0.092 mol) of 2a in 400 mL of anhydrous DMF was added 14.2 g (1.05 equiv.) of phthalimide and 14.4 mL (1.05 equiv.) of 1,8-diazabicyclo[5.4.0] undec-7-ene. The solution was heated at 70° C. for 18 h then concentrated in vacuo. The crude yellow oil was purified by flash chromatography using 1600 mL of silica gel and eluting with 25% EtOAc-50% EtOAc-75% EtOAc in hexane, then EtOAc, then 10% MeOH-20% MeOH in EtOAc to afford 23.8 g (80%) of 3a as an oil. Upon standing, 3a became a waxy white solid. $^1$H NMR (300 MHz, CDCl$_3$) d 7.84–7.78 (m, 2H), 7.70–7.66 (m, 2H), 3.86 (t, J=5.6 Hz, 2H), 3.70 (t, J=5.6 Hz, 2H), 3.64–3.51 (m, 12H), 2.67 (bs, 1H); $^{13}$C NMR (75 MHz, CDCl$_3$) d 168.2, 133.8, 132.0, 123.1, 72.4, 70.5, 70.4, 70.2, 70.0, 67.8, 61.6, 37.2.

Synthesis of compound 4a: A solution of 15 g (0.0464 mol) of 3a in 150 mL of THF and 15 mL of DMF was cooled to 0° C. under Ar. Allyl bromide (6.0 mL, 1.5 equiv.) was added to the solution, followed by addition of 1.76 g (1.5 equiv.) of NaH as a solid. The opaque yellow suspension was stirred at 0° C. for 30 minutes and then at room temperature for 18 hr. MeOH (50–100 mL) was added and concentrated then mixture was concentrated in vacuo. The crude material was purified by flash chromatography using 1500 mL of silica gel and eluting with 25% EtOAc-50% EtOAc-75% EtOAc in hexane, then EtOAc, then 10% MeOH in EtOAc to afford 11.05 g (65%) of 4a as a yellow oil. $^1$H NMR (300 MHz, CDCl$_3$) d 7.84–7.80 (m, 2H), 7.72–7.67 (m, 2H), 5.94–5.84 (m, 1H), 5.28–5.14 (m, 2H), 3.99 (d, J=5.61 Hz, 2H), 3.88 (t,J=5.85 Hz, 2H), 3.72 (t, J=5.76 Hz, 2H), 3.64–3.54 (m, 13H); $^{13}$C NMR (75 MHz, CDCl$_3$) d 168.0, 134.6, 133.7, 131.9, 123.0, 116.9, 72.0, 70.4, 69.9, 69.2, 67.7, 37.0.

1-Dimethoxytrityl-3—(phthalimidotetra ethylene glycolyl)-sn-glycerol (9): According to Scheme 1, compound 9 was synthesized as follows: To a stirred solution of 4a (10.13 g, 0.0279 mol) in 100 mL of acetone and 1 mL of H$_2$O was added 3.98 g (1.22 equiv.) of N-methylmorpholine N-oxide. To this suspension was added 1.75 mL (0.005 equiv.) of Osmium tetroxide as a 2.5% solution in iPrOH. After addition of the OsO$_4$ solution, the reaction mixture became clear yellow. After TLC analysis indicated complete conversion of 4a (ca 16 h), the reaction mixture was treated with 1.5 g of sodium hydrosulfite and 5.0 g of florisil and stirred 30 minutes. The suspension was filtered through florisil, the filtrate was concentrated to an oil. This crude product was combined with another batch prepared in the same manner from 1.0 g of 4a. Two 100 mL portions of pyridine were co-evaporated from the combined lots and the residue was dissolved in 300 mL pyridine. The solution was cooled to 0° C. and 10.89 g (1.05 equiv.) of 4,4'-dimethoxytrityl chloride was added. A drying tube was inserted in the flask and the reaction mixture was stirred at room temperature 16 h. The solution was treated with 20 mL of MeOH and concentrated in vacuo, keeping the temperature of the water bath below 40° C. The crude oil was purified by flash chromatography using 1100 mL of silica gel (wet-packed onto column using 3% triethylamine in hexane) and eluting with 10–100% EtOAc in hexane (all containing 3% triethylamine) to give 21.3 g (89% after two steps) of 9 as a yellow oil. $^1$H NMR (300 MHz, CDCl$_3$) d 7.80–7.77 (m, 2H), 7.66–7.64 (m, 2H), 7.39–7.22 (m, 9H), 7.20–6.76 (m, 4H), 3.97 (bs, 1H), 3.84 (t, J=5.97 Hz, 2H), 3.74 (s, 6H), 3.68 (t, J=5.7 Hz, 2H), 3.60–3.49 (m, 14H), 3.13–2.76 (m, 2H), 2.00 (bs 1H); $^{13}$C NMR (75 MHz, CDCl3) d 168.2, 158.3, 144.8, 135.9, 133.8, 132.0, 129.9, 128.0, 127.7, 126.6, 123.1, 113.0, 85.9, 73.0, 70.6, 70.4, 70.0, 69.7, 67.8, 64.4, 55.1, 37.1; Low resolution MS m/e calculated for C$_{40}$H$_{45}$O$_{10}$N (M+NH$_4$+): 717.5.

1-Dimethoxytrityl-3-(aminotetraethylene glycolyl)-sn-glycerol (10):

According to Scheme 1, compound 10 was synthesized as follows: Compound 9 (5.2 g, 7.2 mmol) was taken up in 50 mL of 40% methylamine in $H_2O$ and 10 mL of methanol was added to solubilized the starting material. The reaction mixture was heated at 50° C. for 5 hr, and than was concentrated in vacuo and coevaporated with toluene. The crude material was purified by flash chromatography on 200 mL of silica gel, eluting with 15% methanolic ammonia in dichloromethane. Collected 3.94g (96%) of 10 as a pale yellow oil. $^1H$ NMR (300 MHz, $CDCl_3$) d 7.46–7.21 (m, 9H, DMT), 6.81 (d, 4H, DMT), 4.00 (m, 1H), 3.80 (s, 6H), 3.70–3.49 (overlapping m, 18H), 3.20 (dd, J=9.24, 5.49 Hz, 1H), 3.12 (dd, J=9.21, 6.0 Hz, 1H), 2.84–2.80 (m, 3H); $^{13}C$ NMR (75 MHz, $CDCl_3$) d 158.30, 144.82, 136.01, 129.95, 128.04, 127.66, 126.61, 112.95, 85.85, 73.46, 72.85, 70.55, 70.45, 69.99, 69.51, 64.43, 55.10, 41.40; Low resolution MS m/e calculated for $C_{32}H_{44}O_8N$ ($M+1^+$): 570.353, found 570.4.

the combined lots purified by flash silica gel chromatography on a column of 100 mL of silica gel (packed in hexanes containing 2% triethylamine) eluting withn 200 mL hexanes, then 250 mL each of 10–20 and 30% EtOAc in hexanes, 500 mL 40% EtOAc in hexanes, then 250 mL each of 50–60–70 and 80% EtOAc in hexanes, and finally with 250 mL of EtOAc. The product containing fractions were concentrated to afford 3.3 g (57%) of the conjugate 20.

Phosphoramidite 21: To a stirred solution of 3.8 g (3.26 mmol) of the conjugate in 25 mL of $CH_2Cl_2$ was added 1.14 mL (6.52 mmol) of diisopropylethylamine then 1.09 mL (4.88 mmol) of 2-cyanoethyl N,N-diisopropylchlorophosphoramidite. After 2 hours, the mixture was diluted with $CH_2Cl_2$ and washed with saturated $NaHCO_3$ solution, dried over $Na_2SO_4$, and concentrated. The crude residue was purified by flash silica gel chromatography on a column of 125 mL of silica gel (packed in hexanes containing 2% triethylamine) eluting with 100 mL hexanes, then 250 mL each of 10 and 20% EtOAc in hexanes, 500 mL 30% EtOAc in hexanes, then 250 mL of 50% EtOAc in hexanes. The

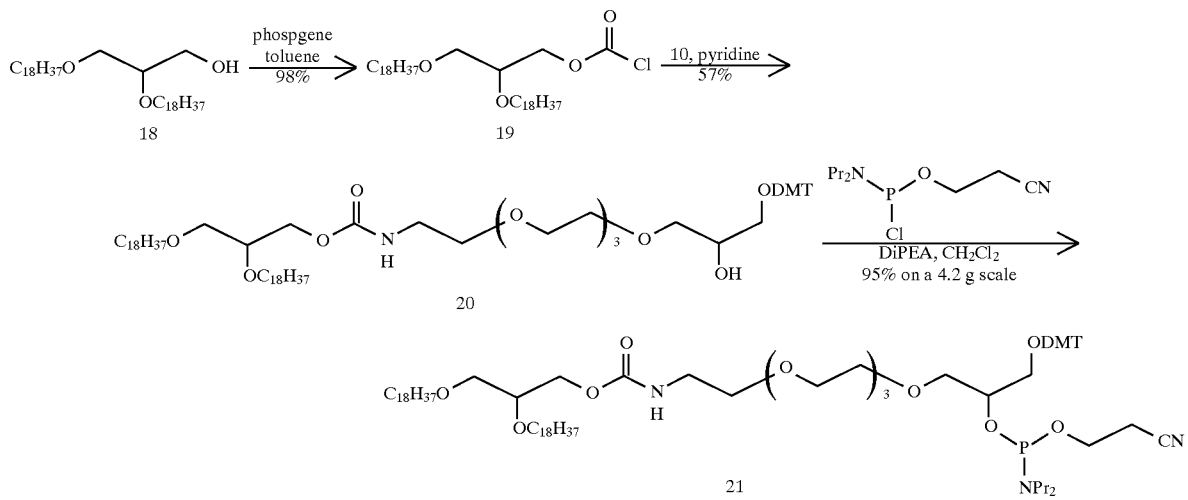

Scheme 2

Chloroformate 19: To a stirred solution of 3 g (5.03 mmol) of 1,2-di-O-octadecyl-sn-glycerol 18 in 60 mL of toluene was added 20 mL of a 1.93 M solution of phosgene. Additional phosgene solution (2×10 mL; 15.4 equiv phosgene total) was added until no further alcohol starting material remained (by $^1H$ NMR analysis of concentrated aliquots). The excess phosgene and HCl was removed by aspirator and the reaction mixture was concentrated in vacuo to afford 3.3 g (98%) of the desired chloroformate 19 as a white powder. $^1H$ NMR (300 MHz, $CDCl_3$) d 4.45 (dd, J=11.22, 3.69 Hz, 1H), 4.34 (dd, J=11.22, 6.15 Hz, 1H), 3.65 (m, 1H), 3.56–3.40 (m, 6H), 1.53 (m, 4H), 1.24 (m, 62H), 0.87 (t, J=6.36 Hz, 6H); $^{13}C$ NMR (75 MHz, $CDCl_3$) d 75.90, 71.91, 71.35, 70.93, 69.36, 31.99, 29.96–29.44 (overlapping signals from hydrocarbon chains), 26.13, 26.04, 22.76, 14.18.

Conjugate 20: To a stirred solution of 2.25 g (3.95 mmol) of 10 in 60 mL of pyridine was added 2.6 g of the distearyl glycerol chloroformate 19. $^1H$ NMR analysis of a concentrated aliquot after 2 h revealed no remaining chloroformate and the mixture was concentrated in vacuo. The crude residue was combined with material similarly prepared from 0.5 g (0.88 mmol) of 10 and 0.58 g of the chloroformate and product containing fractions were concentrated to afford 4.2 g (95%) of the phosphoramidite 21. $^{31}P$ NMR ($CDCl_3$) δ 151.52, 151.08.

The VEGF Nucleic Acid Ligand-1,2-di-O-octadecyl-sn-glycerol conjugate

Figure 1C:
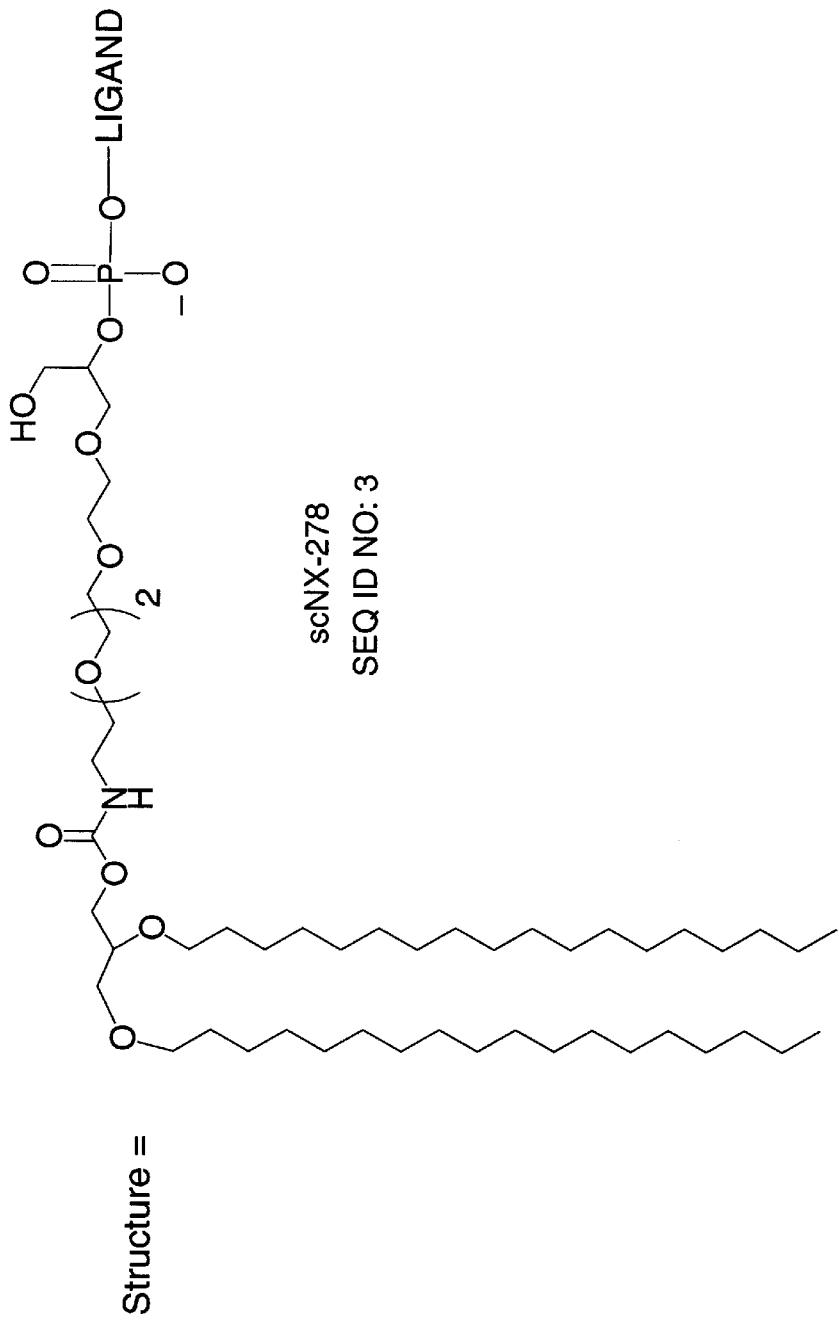

The 1,2-di-O-octadecyl-sn-glycerol group was conjugated to VEGF Nucleic Acid Ligand NX213 (See FIG. 1A; SEQ ID NO: 1) using phosphoramidite 21 (Scheme 2). The resulting conjugate was named NX278 (See FIG. 1B; SEQ ID NO: 2). NX278 was purified by reverse phase HPLC and its composition was confirmed by electrospray mass spectroscopy (m/z observed=11703±4, m/z calculated=11720). Phosphorothioate internucleoside linkages were used at 8 positions in NX278 (at the 3' and 5' ends) and the difference of ≈16 mass units between the expected and observed masses is probably due to incomplete oxidation by the sulfurizing agent resulting, on average, in one less phosphorothioate linkage per molecule than expected.

EXAMPLE 2

In vitro and in vivo efficacy of Nucleic Acid Ligand-Liposome Complex. Dialkylglycerol (DAG)-modified VEGF Nucleic Acid Ligand (NX278) embedded in Liposome bilayer NX278-Liposome Complex was prepared by incubating NX-278 (1 mg) (FIG. 1B; SEQ ID NO: 2) with a spray-dried mixture of DSPC:cholesterol (50 mg/ml; 2:1, Mol:Mol) in 25 mM phosphate (pH 7.4) buffer containing 9% sucrose and sonicated for 15–30 min at approximately 60° C. using a probe-type sonicator until opalescent solution was obtained. The control Nucleic Acid Ligand-Liposome Complex containing a sequence scrambled analog of ligand NX-278 (scNX278) (FIG. 1C; SEQ ID NO:3 ) was prepared in the same manner. In a typical preparation, liposomes with a mean diameter of ≈50 nm and a distribution width at half height of ≈20 nm were obtained. The size of Liposome particles was determined in a particle analyzer (Leeds & Northrup Model Microtrack UPA 150, Horsham, Pa.). Liposomes of comparable size distribution were obtained with the same lipid composition but without the lipid-conjugated Nucleic Acid Ligand. A 50 nm liposome is expected to contain an average of ≈40 Nucleic Acid Ligands, displayed on both sides of the bilayer. The calculation was made as follows. Assuming a surface area of 19 Å for cholesterol and 60 Å for distearoyl phoshatidylcholine in the liposome, a number of lipid molecules per liposome of $3.13 \times 10^4$ was obtained, for a spherical liposome with 50 nm outer diameter and membrane thickness of 20 Å. From the composition of the liposome (2:1 mol:mol disteariphosphatidylcholine (MW=790.2):cholesterol (MW=386.7), assuming homogeneous distribution of lipids, molecular mass of $\approx 2.1 \times 10^7$ for the liposome was calculated.

To determine the partitioning of the Nucleic Acid Ligands between the inside and outside surfaces of liposomes, the accessibility of NX278 (SEQ ID NO: 2) in the liposomal formulation to $T_1$ ribonuclease was examined. With two riboguanosines in the sequence (Green et al. (1995) Chemistry and Biology 2:683–695), NX278 is efficiently cleaved by ribonuclease $T_1$. Simple incubation of NX278 with preformed liposomes does not protect the Nucleic Acid Ligand from ribonuclease $T_1$. However, when NX278 is incorporated in liposomes by sonication (NX278-Liposome), about ⅓ is protected from the nuclease. The addition of 0.1% triton X-100 to NX278-Liposome, which disrupts the liposomes without affecting the activity of the nuclease, exposes the previously protected Nucleic Acid Ligand to digestion. These results are consistent with the notion that the Nucleic Acid Ligand is distributed on both sides of the bilayer.

Binding affinities of NX213, NX278, and NX278-Liposome for VEGF

Figure 2:
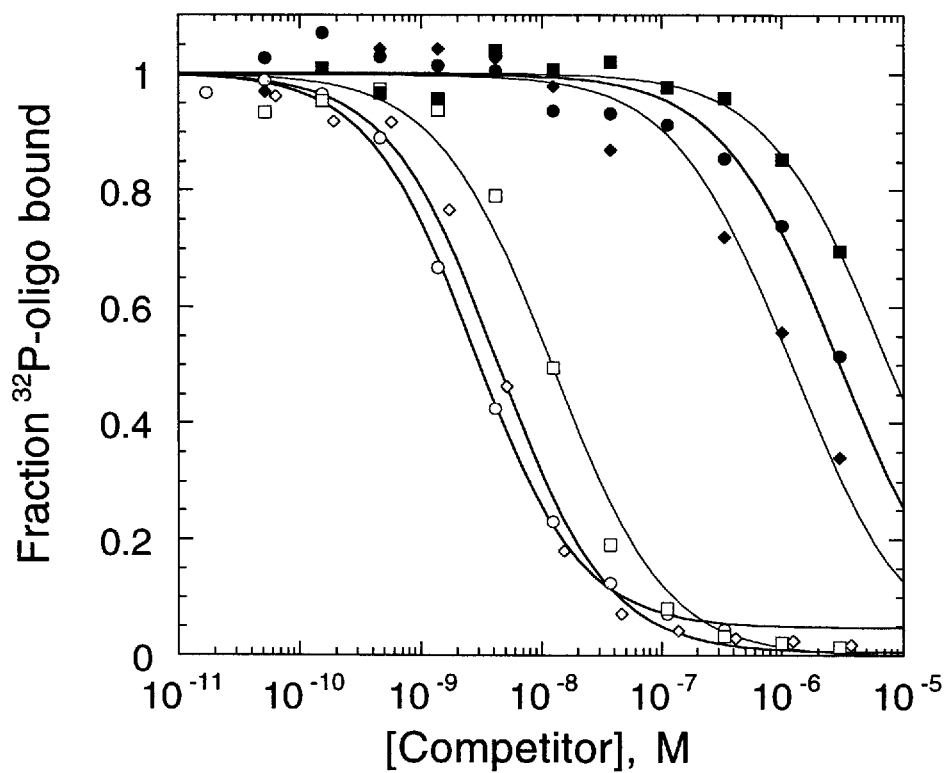
FIG. 2 shows binding properties of various Nucleic Acid Ligands to VEGF. The binding affinities of the unmodified Nucleic Acid Ligand (NX213, open circle), its dialkyl glycerol modified analog (NX278, open diamond) and liposomal NX278 (NX278-L, open square), along with the sequence scrambled (sc) controls (scNX213, closed circle; scNX278, closed diamond; and scNX278-L, closed square) were determined by a competition electrophoretic mobility shift assay. NX213 is 5'-TsTsTsTs (SEQ ID NO: 1) mAaCaC aCaUrG rAaUmG rGaUrnA mGrAaC mGaCaC mGmGmG mGaUmG TsTsTsTsT-3' and scNX213 is 5'-TsTsTsTs(SEQ ID NO:1) mGaUaC mGmGaU mAaCrG mGrAmG aUmGrG rAaCnC mGaUaC mAaCmG TsTsTsTsT-3'(SEQ ID NO:4) $^{32}$P 5' end-labeled NX-213 (1.5 nM) was incubated in binding buffer (phosphate buffered saline with 0.01% human serum albumin) at 37° C. for 20 min in the presence of VEGF (0.33 nM) and competitor oligonucleotide (5 µM-0.33 µM). The $^{32}$P NX-213/VEGF complex was resolved from the free $^{32}$P NX-213 by electrophoresis on 8% polyacrylamide gel (19:1 acrylamide:bis-acrylamide, Trisborate, 89 mM, 1 mM EDTA as the running buffer). The intensity of the band corresponding to $^{32}$P NX-213/VEGF complex at varying competitor concentrations was, quantitated by phosphorimager analysis. Data normalized for the amount of complex formed in the absence of competitor were fitted by the least squares method to the competition binding equation.

The binding affinities of NX213(SEQ ID NO: 1), NX278 (SEQ ID NO: 2) and NX278-Liposome for VEGF was examined using a competition electrophoretic mobility shift method (FIG. 2). The binding affinity of NX278 for VEGF was comparable to that of NX213. The apparent binding affinity of NX278-Liposome was ≈3-fold lower compared with NX278. A part of the observed affinity reduction is potentially due to the confinement of a fraction of the Nucleic Acid Ligand to the liposome interior. As expected, the sequence scrambled analogs bind to VEGF with substantially lower affinities (FIG. 2).

The Effect of NX278 on HUVEC proliferation and angiogenesis

The effects of NX278-liposome, scNX278-liposome and NX213 on the proliferation of human umbilical vein endothelial cells (HUVEC) was examined. HUVECs were grown in the presence of VEGF (10 ng/ml) in IMDM:Ham's F12 (1:1) medium containing 10% fetal calf serum (FCS) and heparin (45 µg/ml). Cells were plated in 24-well gelatin-coated plates at a density of 20,000 cells per well on day zero and treated with the above ligands at concentrations between 0.1 nM to 1 µM on days 1, 2, and 3 (replacing the media along with the ligands. NX278-Liposome inhibited the proliferation of HUVECs with an IC50 of ≈300 nM (the concentration refers to the Nucleic Acid Ligand component); scNX278-Liposome and NX213 were significantly less effective (IC50>1 µM).

VEGF induces angiogenesis in chicken allantoic membrane (CAM) assays, and this assay can be utilized to study compounds that inhibit angiogenesis. The assay is done by placing filter discs soaked in VEGF on the CAM and the development of new blood vessels can be quantitated. NX278-Liposome effectively blocked VEGF induced angiogenesis (data not shown), while NX213 (SEQ ID NO: 1), NX:278 (SEQ ID NO: 2), and scNX278-Liposome had no effect. Together these studies demonstrate that NX278 is a specific inhibitor of VEGF induced endothelial cell proliferation in vitro and new vessel formation in vivo.

Effect of NX278 on VEGF induced capillary permeability

Figure 3:
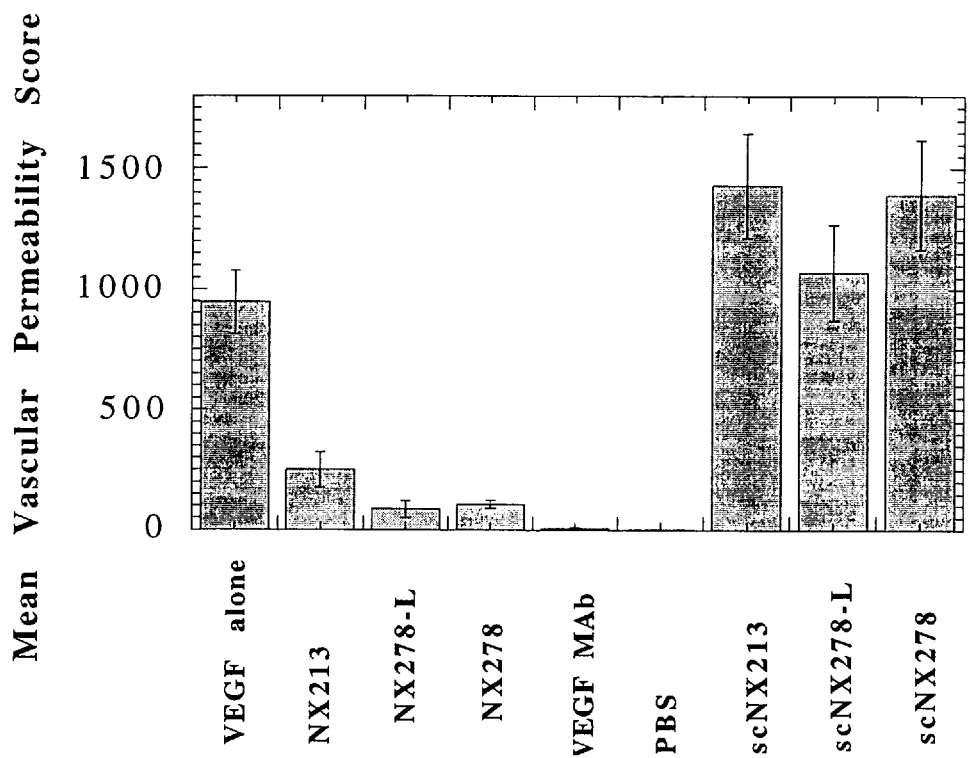
FIG. 3 shows the effect of various Nucleic Acid Ligands on VEGF-induced increases in vascular permeability. VEGF (20 nM) with or without Nucleic Acid Ligands was injected intradermally to guinea pigs that had previously received an injection of Evans blue dye. The amount of dye leakage was quantitated by measuring the relative amount of light absorbed by the skin at the site of injection.

VEGF is the only known angiogenic factor that transiently enhances capillary permeability. The ability of NX278-Liposome to inhibit the vascular permeability activity of VEGF in vivo was examined. The vascular permeability assay (also known as the Miles assay (Miles, A. A. and Miles, E. M. (1952) *J. Physiol.* (London) 118:228) was performed in guinea pigs essentially as described (Senger, R. S. et al., (1983) *Science* 25 219:983). NX278-Liposome, NX278, and NX213 at the concentration of 1 µM were injected intradermally with VEGF (20 nM) in guinea pigs preinjected with Evans blue dye. In response to VEGF, an increase in vascular permeability causes extravasation of albumin-bound Evans blue dye resulting in a blue spot at the site of injection. Because the recovery of the dye by organic solvent extraction is generally very poor, a quantitation method has been developed that measures the absorption of light through the skin. NX213, NX278, NX278-Liposome and neutralizing monoclonal antibody to VEGF all significantly inhibited VEGF-induced permeability as shown in FIG. 3. Among the Nucleic Acid Ligands, NX278-Liposome appeared to be the most potent antagonist. Sequence scrambled analogs of these compounds were not inhibitory. The differences were dramatic and noticeable to the naked eye.

NX278-L inhibits Kaposi's sarcoma cell lines in vitro

Inhibitors of VEGF have a potential utility in a variety of diseases, including malignancies where tumor progression and metastasis are dependent on new vessel formation. While most tumor types are known to produce VEGF, previously none has been shown to express functional VEGF receptors. It has been shown recently that Kaposi's sarcoma (KS) cells not only produce abundant amounts of VEGF but also express functional VEGF receptors and therefore use VEGF for autocrine growth. KS cell lines thus provide a unique opportunity to examine the ability of NX278 to interrupt the autocrine VEGF growth activity.

Figure 4:
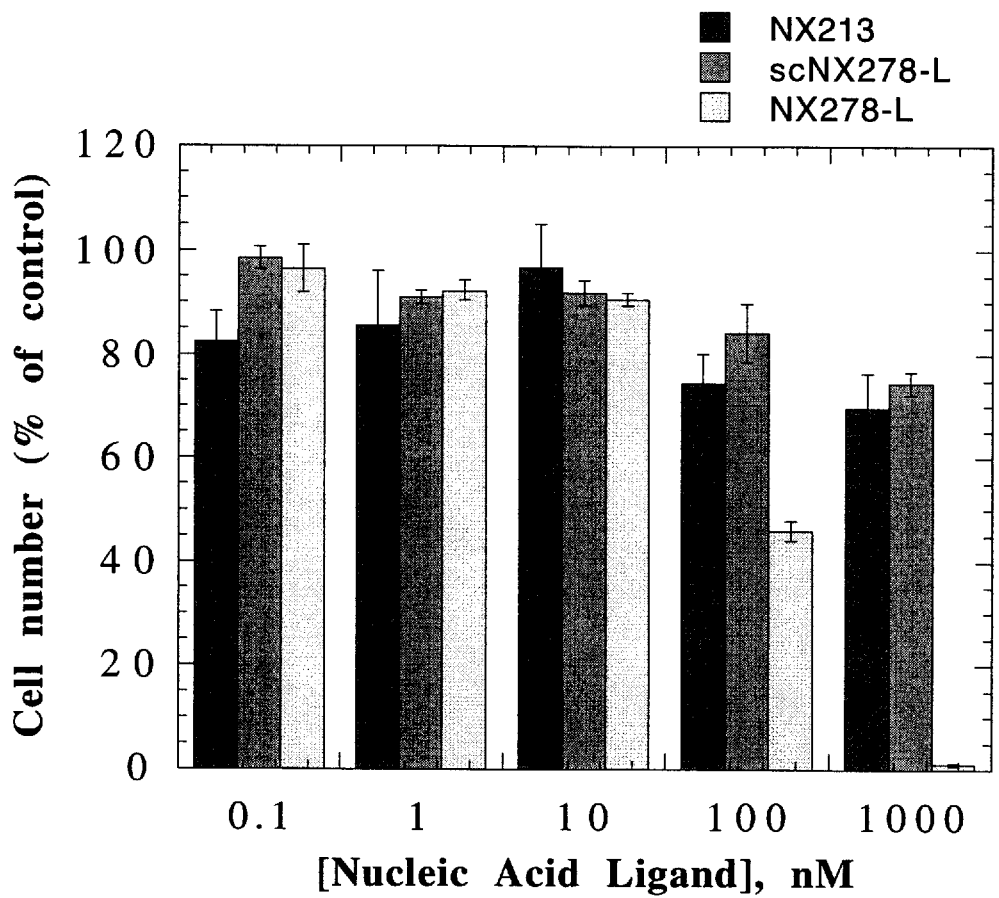
FIG. 4 shows that NX278-L inhibits KS cell growth. Growth of KSY-1 cells in the presence of various concentrations of NX213, NX278-L and scNX278-L. KSY-1 cells were seeded in 24 well plates at a density of 1×10$^4$ cells/well on day 0. Fresh medium treated identically was replaced on days 1 and 3. The cell numbers were determined by trypsinization of cells on day 5 or 6 of culture using particle coulter counter. The experiments were done in triplicate several times. Results shown are the average and SE of representative experiment.

The effects of NX278-Liposome, scNX278-Liposome and NX213 on the proliferation of KS cells was examined. KS cell line KSY-1 was plated in 24-well gelatin coated plates at a density of 7,500–10,000 cells per well on day zero in medium containing RPMI 1640 supplemented with 2% FCS, L-glutamine, penicillin and streptomycin. Nucleic Acid Ligands were added at concentrations between 0.1 nM to 1 µM in fresh medium on day 1, 2, and 3 and the cell count was performed on day 4. NX278-Liposome inhibited the proliferation of KS cells with an IC50 of ≈100 nM; at 1 µM NX278-Liposome, the growth of these cells was completely inhibited. scNX278-25 Liposome and NX213 exhibited IC50 values of >1 μM (FIG. 4).

NX278-Liposome inhibits KS cell growth in vivo

Figure 5A:
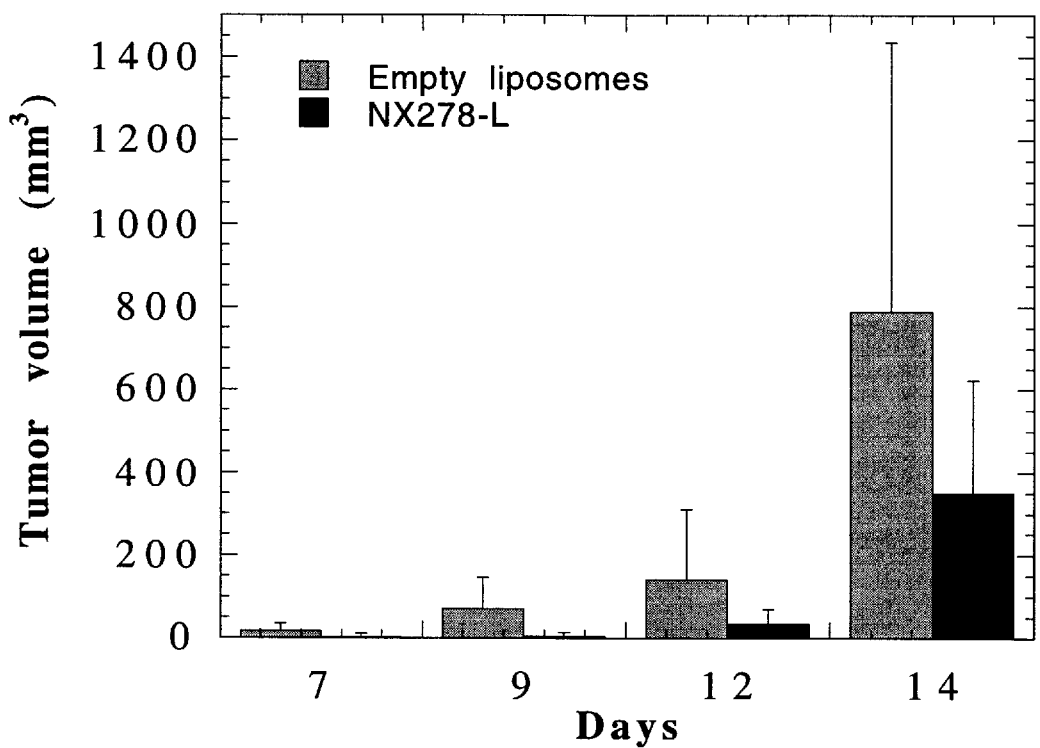
FIGS. 5A and 5B show that NX278 (SEQ ID NO:2) inhibits KS cell growth in athymic mice. Athymic mice were implanted with KS tumor behind the forlegs on day 1. Mice were treated with NX278-L (50 µg/day/mouse, FIG. 5A and 150 µg/day/mouse, FIG. 5B) by intraperitoneal injection daily for five days beginning on day 2. Control mice were treated with empty liposomes using the same quantity of lipids as the Nucleic Acid Ligand treated group. The tumor sizes were measured over the period of two weeks. The tumors were removed on day 14 and measured.
Figure 5B:
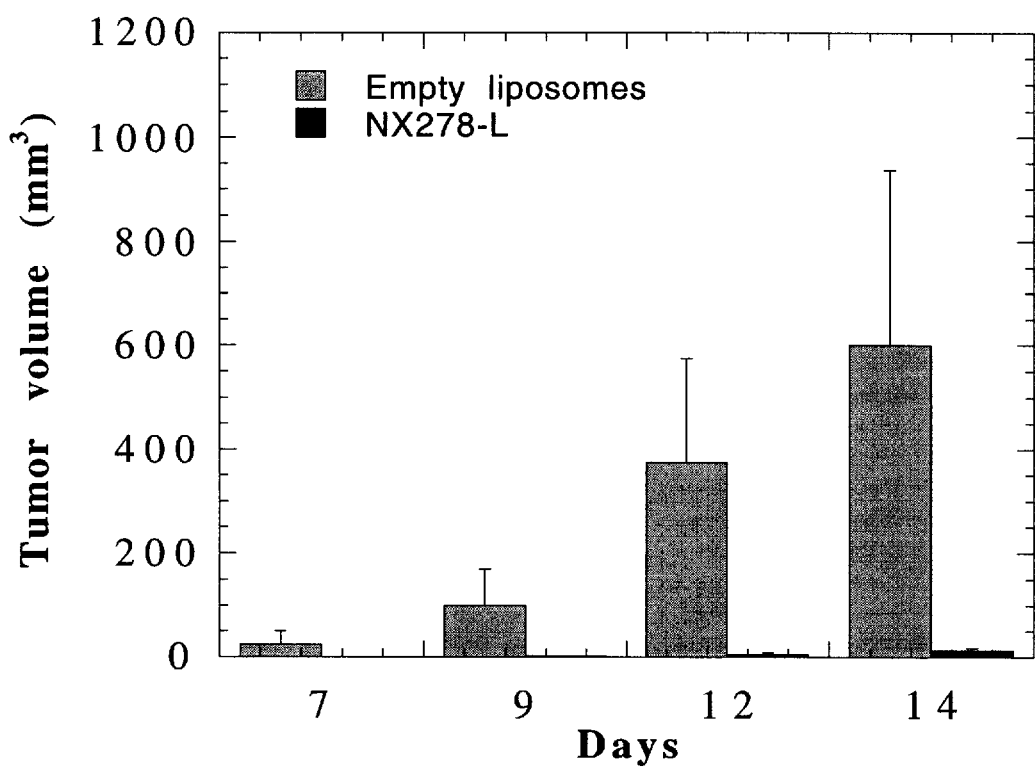

Because VEGF is a growth factor for KS cells, the effect of VEGF antagonists on KS tumors in vivo is likely to be two-fold: inhibition of paracrine growth effect of VEGF on tumor associated endothelial cells and inhibition of autocrine growth effect on tumor cells. KS tumors may thus be particularly sensitive to VEGF antagonists. To test the activity of the Nucleic Acid Ligands in vivo, tumor trocars (≈3 mm$^3$) were implanted in athymic mice on day one and treated for five consecutive days beginning on day two with 50, 100 or 150 μg/day/mouse. The rate of tumor growth was measured for a period of two weeks. NX278-Liposome inhibited the tumor growth in a dose dependent marner with very little inhibition of tumor growth at the lowest dose level of 50 μg/day/mouse dose (FIG. 5A), and marked inhibition of tumor growth at both 100 and 150 μg/day/mouse dose levels (FIG. 5B, 150 μg/day/Aouse shown). Empty liposomes (FIGS. 5A, B), scNX278-Liposome as well as NX213 and NX278 were ineffective at all doses examined. In addition, NX278-Liposome blocked the VEGF-induced fluid leakage from blood vessels.

We claim:

1. A method for the preparation of a Complex comprised of a vascular endothelial growth factor (VEGF) Nucleic Acid Ligand and a Lipophilic Compound, said method comprising:
   a) contacting the Candidate Mixture with VEGF, wherein Nucleic Acids having an increased affinity to VEGF relative to the Candidate Mixture may be partitioned from the remainder of the Candidate Mixture;
   b) partitioning the increased affinity VEGF Nucleic Acids from the remainder of the Candidate Mixture;
   c) amplifying the increased affinity VEGF Nuclcic Acids to yield a ligand-enriched mixture of Nucleic Acids; and
   d) covalently linking said identified VEGF Nucleic Acid Ligand with a Lipophilic Compound.

2. The method of claim 1 wherein said Lipophilic Compound is a lipid.

3. The method of claim 2 wherein said lipid is selected from the group consisting of dialkylglycerol and diacyiglycerol.

4. The method of claim 1 wherein said Complex is further associated with a Lipid Construct.

5. The method of claim 4 wherein said Lipid Construct is a Lipid Bilayer Vesicle.

6. The method of claim 5 wherein said Lipid Bilayer Vesicle is a Liposome.

7. A method for preparing a Lipid Construct comprising a Complex comprised of a VEGF Nucleic Acid Ligand and a Lipophilic Compound, said method comprising:
   a) contacting the Candidate Mixture with VEGF, wherein Nucleic Acids having an increased affinity to VEGF relative to the Candidate Mixture may be partitioned from the rermainider of the Candidate Mixture;
   b) partitioning the increased affinity VEGF Nucleic Acids from the remnainder of the Candidate Mixture;
   c) amplifying the increased affinity VEGF Nucleic Acids to yield a ligand-enriched mixture of Nucleic Acids;
   d) covalently linking said identified VEGF Nucleic Acid Ligand with a Lipophilic Compound to form a Complex; and
   e) forming a Lipid Construct comprising said Complex.

* * * * *

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: Bases at positions 1-4 and 29-33
            are bound by a phosphorothioate bond ( i x ) FEATURE:
        ( D ) OTHER INFORMATION: Bases at positions 5, 13, 16,
            17, 20, 23- 26, and 28 are 2'-OMe modified ( i x ) FEATURE:
        ( D ) OTHER INFORMATION: Bases at positions 6-9, 12, 15,
            19, 21, 22 and 27 are 2'-NH2 modified ( x i ) SEQUENCE DESCRIPTION: SEQ ID NO: 1:

TTTTACCCUG AUGGUAGACG CCGGGGUGTT TTT        3 3

( 2 ) INFORMATION FOR SEQ ID NO: 2:

( i ) SEQUENCE CHARACTERISTICS:
        ( A ) LENGTH: 33
        ( B ) TYPE: nucleic acid
        ( C ) STRANDEDNESS: single
        ( D ) TOPOLOGY: linear ( i i ) MOLECULE TYPE: RNA ( i x ) FEATURE:
        ( D ) OTHER INFORMATION: Bases at positions 1-4 and 29-33
            are bound by a phosphorothioate bond ( i x ) FEATURE:
        ( D ) OTHER INFORMATION: Bases at positions 5, 13, 16-17,
            20, 23-26, and 28 are 2'-OMe modified ( i x ) FEATURE:
        ( D ) OTHER INFORMATION: Bases at positions 6-9, 12, 15,
            19, 21-22 and 27 are 2'-NH2 modified ( x i ) SEQUENCE DESCRIPTION: SEQ ID NO: 2:

TTTTACCCUG AUGGUAGACG CCGGGGUGTT TTT        3 3

( 2 ) INFORMATION FOR SEQ ID NO: 3:

```
        ( i ) SEQUENCE CHARACTERISTICS:
                ( A ) LENGTH: 33
                ( B ) TYPE: nucleic acid
                ( C ) STRANDEDNESS: single
                ( D ) TOPOLOGY: linear ( i i ) MOLECULE TYPE: RNA ( i x ) FEATURE:
                ( D ) OTHER INFORMATION: Bases at positions 1-4 and 29-33
                        are bound by a phosphorothioate bond ( i x ) FEATURE:
                ( D ) OTHER INFORMATION: Bases at positions 5, 8-9, 11,
                        14, 16, 18, 23, 26, and 28 are 2'-OMe modified ( i x ) FEATURE:
                ( D ) OTHER INFORMATION: Bases at positions 6-7, 10, 12,
                        17, 21-22, 24-25, and 27 are 2'-NH2 modified ( x i ) SEQUENCE DESCRIPTION: SEQ ID NO:3:

TTTTGUCGGU  ACGGAGUGGA  CCGUCACGTT  TTT                                          3 3

( 2 ) INFORMATION FOR SEQ ID NO: 4:

( i ) SEQUENCE CHARACTERISTICS:
                ( A ) LENGTH: 33
                ( B ) TYPE: nucleic acid
                ( C ) STRANDEDNESS: single
                ( D ) TOPOLOGY: linear ( i i ) MOLECULE TYPE: RNA ( i x ) FEATURE:
                ( D ) OTHER INFORMATION: Bases at positions 1-4 and 29-
                        33 are bound by a phosphorothioate bond ( i x ) FEATURE:
                ( D ) OTHER INFORMATION: Bases at positions 5, 8-9, 11,
                        14, 16, 18, 23, 26, and 28 are 2'-OMe modified ( i x ) FEATURE:
                ( D ) OTHER INFORMATION: Bases at positions 6-7, 10, 12,
                        17, 21-22, 24-25, and 27 are 2'-NH2 modified ( x i ) SEQUENCE DESCRIPTION: SEQ ID NO:4:

TTTTGUCGGU  ACGGAGUGGA  CCGUCACGTT  TTT                                          3 3
```